(12) United States Patent
Haller et al.

(10) Patent No.: US 11,684,370 B2
(45) Date of Patent: Jun. 27, 2023

(54) CRISS-CROSS CORDS FOR BAND LIGATION

(71) Applicant: United States Endoscopy Group, Inc., Mentor, OH (US)

(72) Inventors: Frederick Barclay Haller, Clemmons, NC (US); Melissa Hagerman Haller, Clemmons, NC (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 83 days.

(21) Appl. No.: 17/043,150

(22) PCT Filed: Mar. 29, 2019

(86) PCT No.: PCT/US2019/024849
§ 371 (c)(1),
(2) Date: Sep. 29, 2020

(87) PCT Pub. No.: WO2019/191595
PCT Pub. Date: Oct. 3, 2019

(65) Prior Publication Data
US 2021/0145443 A1    May 20, 2021

Related U.S. Application Data

(60) Provisional application No. 62/650,828, filed on Mar. 30, 2018.

(51) Int. Cl.
*A61B 17/12* (2006.01)
*A61B 17/00* (2006.01)

(52) U.S. Cl.
CPC ........... *A61B 17/12013* (2013.01); *A61B 2017/00269* (2013.01); *A61B 2017/00296* (2013.01); *A61B 2017/12018* (2013.01)

(58) Field of Classification Search
CPC .......... A61B 2017/00296; A61B 2017/12018; A61B 17/12009; A61B 17/12013;
(Continued)

(56) References Cited

U.S. PATENT DOCUMENTS 5,398,844 A * 3/1995 Zaslavsky ........ A61B 17/12013
606/140
5,423,834 A * 6/1995 Ahmed ............ A61B 17/12013
606/139
(Continued)

FOREIGN PATENT DOCUMENTS

EP    0773741     5/1997
EP    2136719    12/2009
(Continued)

OTHER PUBLICATIONS

Extended Search Report from European Application No. 19774335.4 dated Nov. 12, 2021 (5 pages).
(Continued)

*Primary Examiner* — Kathleen S Holwerda
*Assistant Examiner* — Serenity A Miller
(74) *Attorney, Agent, or Firm* — Calfee, Halter & Griswold LLP

(57) ABSTRACT

Devices, methods, and systems are provided for consistent and effective delivery of ligating bands. In one embodiment, a crisscross orientation of pull cords along an exterior surface of a ligation barrel can be used to ensure consistent delivery of ligation bands to tissue, resulting in better results for patients and an easier, safer operation for users.

18 Claims, 22 Drawing Sheets

(58) Field of Classification Search
CPC .......... A61B 2017/306; A61B 1/00101; A61B 1/00087; A61B 17/12–12022
USPC ........................................................ 606/140
See application file for complete search history.

(56) References Cited

U.S. PATENT DOCUMENTS

| | | | | |
|---|---|---|---|---|
| 5,462,559 | A * | 10/1995 | Ahmed | A61B 17/12013 606/139 |
| 5,624,453 | A * | 4/1997 | Ahmed | A61B 17/12013 606/139 |
| 5,857,585 | A * | 1/1999 | Tolkoff | A61B 17/12013 221/36 |
| 6,007,551 | A * | 12/1999 | Peifer | A61B 17/12013 606/139 |
| 6,235,040 | B1 * | 5/2001 | Chu | A61B 17/12013 606/139 |
| 9,119,622 | B2 | 9/2015 | Rahmani | |
| D859,659 | S | 9/2019 | Clark et al. | |
| 2001/0014810 | A1 | 8/2001 | Chu et al. | |
| 2002/0072757 | A1 | 6/2002 | Ahmed et al. | |
| 2004/0006256 | A1 * | 1/2004 | Suzuki | A61B 1/00133 600/140 |
| 2013/0274766 | A1 | 10/2013 | Issacson et al. | |
| 2014/0142596 | A1 * | 5/2014 | Knotts | A61B 17/00234 606/140 |
| 2014/0364873 | A1 * | 12/2014 | Smith | A61B 17/12013 606/140 |
| 2015/0018849 | A1 | 1/2015 | Chami | |
| 2017/0303930 | A1 | 10/2017 | Haller et al. | |

FOREIGN PATENT DOCUMENTS

| | | |
|---|---|---|
| WO | 2016/086003 A1 | 6/2016 |
| WO | 2019191595 A1 | 10/2019 |

OTHER PUBLICATIONS

International Search Report and Written Opinion of International Application No. PCT/US2019/024849 dated Jun. 14, 2019, 9 pages.

* cited by examiner

CRISS-CROSS CORDS FOR BAND LIGATION

CROSS-REFERENCE TO RELATED APPLICATIONS

This application claims the benefit of priority to PCT Application No. PCT/US2019/024849, filed on Mar. 29, 2019, and to U.S. Provisional Application 62/650,828, filed on Mar. 30, 2018. The entire contents of these applications are incorporated herein by reference in their entirety.

FIELD

Devices, methods, and systems are provided for band ligation, and especially for consistent and effective ligation band deployment.

BACKGROUND

Endoscopic treatment of lesions is presently being accomplished through a variety of techniques. One technique involves ligation of lesions, in which mucosal and/or submucosal tissue is strangulated by an elastic band. Common current methods of performing this technique are variceal ligation and mucosal resection, which both use band ligation devices.

Band ligation delivery systems generally consist of a ligation barrel, one or more pull cords, and one or more ligation bands. The one or more pull cords extend distally through a lumen in the ligation barrel, loop around a distal end of the ligation barrel, and then extend proximally along an exterior surface of the ligation barrel. The cords each have one or more knots or beads formed thereon at specific locations that are each designed to engage with a corresponding ligation band. Each ligation band is loaded on to the ligation barrel by positioning the band around the ligation barrel and the pull cords. As such, each ligation band holds the cords on the exterior surface of the barrel and is positioned distally to its corresponding beads. As a user retracts the cords proximally through the lumen of the ligation barrel, the beads are pulled distally along the exterior surface of the ligation barrel toward the distal end of the barrel, and each band in turn is pushed distally by the corresponding beads. When the beads reach the distal end of the barrel, the beads loop around the distal end to be pulled proximally through the lumen of the barrel and each corresponding ligation band is sequentially deployed from the distal end of the barrel to capture tissue held by the ligation barrel.

However, devices currently used for these procedures struggle with effective and consistent band deployment around captured tissue, especially using two or more pull cords that extend parallel to each other along the exterior surface of the ligation barrel.

Therefore, a need exists for devices, methods, and systems for band ligation that can deploy bands in an effective, consistent manner.

SUMMARY

In general, devices, methods, and systems are provided for consistent and effective ligation band deployment from band ligation devices.

In one embodiment, a band ligation apparatus is provided that includes an elongate barrel having a proximal end matable to an endoscope, a distal end, and an inner lumen extending through the proximal and distal ends. A plurality of bands are disposed circumferentially around an external surface of the elongate barrel. First and second cords are included, and each cord extends from a terminal trailing end, distally along the external surface of the elongate barrel, around the distal end, and proximally through the inner lumen such that a leading end of each cord extends proximally from the elongate barrel. The first and second cords overlap one another to form a crisscross pattern along the external surface, and the first and second cords have a plurality of beads immovably disposed thereon and positioned between each of the plurality of bands for deploying the bands.

The device can have numerous variations. For example, proximal retraction of the leading end of each of the first and second cords can be configured to cause the plurality of beads to sequentially advance the plurality of bands distally to deploy the bands around tissue drawn into the inner lumen of the elongate barrel. In another example, the elongate barrel can have a horizontal plane extending along a longitudinal axis of the inner lumen and through the distal end defining first and second sides of the elongate barrel, and the crisscross pattern can be formed only on one of the first and second sides of the elongate barrel. In still another example, the crisscross pattern of the first and second cords can include the first and second cords being looped around each other at each point of overlap along the external surface. Each point of overlap by the first and second cords along the external surface can be arranged in a line on the external surface that extends parallel to a longitudinal axis of the inner lumen.

In some embodiments, the distal end of the elongate barrel can have a terminal end surface extending at an oblique angle to a longitudinal axis of the inner lumen such that the terminal end surface has a distal-most point, a proximal-most point, and first and second opposed mid-points positioned equidistant between the distal-most and proximal-most points. The elongate barrel can have a horizontal plane extending along the longitudinal axis of the inner lumen and through the first and second opposed mid-points to define a first horizontal segment of the elongate barrel including the distal-most point, and a second horizontal segment of the elongate barrel including the proximal-most point. In one example, the terminal trailing end of each cord can be positioned on the first horizontal segment of the elongate barrel. Each cord can extend distally from the terminal trailing end along only the first horizontal segment on the external surface of the elongate barrel. In another example, the elongate barrel can include at least one notch formed thereon adjacent the distal end, and the at least one notch can be configured to seat and/or delay a band during deployment of the bands.

In another example, the external surface of the elongate barrel can have at least one lip formed adjacent the distal end of the elongate barrel and configured to engage and delay deployment of each of the plurality of bands. In still another example, the elongate barrel can have at least one tissue-stopping protrusion projecting radially inward from an inner sidewall of the inner lumen.

In another embodiment, a band ligation apparatus can be provided that includes a hollow elongate barrel with a proximal end and a distal end with a terminal surface. First and second cords can extend through the hollow elongate barrel, around the terminal surface, and along an outer surface of the hollow elongate barrel, and the first and second cords can have a plurality of beads immovably disposed thereon. A plurality of bands can be disposed circumferentially around the hollow elongate barrel and the first and second cords, and the plurality of bands can be spaced axially therealong. At least one of the plurality of beads on each of the first and second cords can be positioned between each of the plurality of bands for deploying the bands. The first and second cords can engage one another between each of the plurality of bands along the outer surface.

The apparatus can have numerous variations. For example, the first and second cords can be twisted together as they engage. In another example, the first and second cords can engage one another along the outer surface of the hollow elongate barrel in an approximately straight line parallel to a longitudinal axis of the hollow elongate barrel.

In some embodiments, the terminal surface of the hollow elongate barrel can have one of an oblique angle and a perpendicular angle relative to a longitudinal axis of the hollow elongate barrel. In another example, the hollow elongate barrel can have at least one ledge projecting radially inward from an inner sidewall of the hollow elongate barrel. In another example, proximal retraction of the leading end of each of the first and second cords can be configured to cause the plurality of beads to sequentially advance the plurality of bands distally to deploy the bands around tissue drawn into the inner lumen of the elongate barrel.

In another embodiment, a method for loading a plurality of bands onto a ligation barrel is provided that includes positioning a first bead on a terminal end of a first cord at a first location on an outer surface of a ligation barrel, and positioning a second bead on a second cord at a second location on the outer surface of the ligation barrel. The first and second locations are spaced equidistant from a distal end of the ligation barrel relative to each other and are spaced circumferentially from each other on the ligation barrel. The method also includes advancing a first band onto the ligation barrel to position the first band distally adjacent the first and second beads. After advancing the first band onto the ligation barrel, the method includes crossing the first and second cords at least once. The method further includes positioning a third bead on the first cord longitudinally distal to one of the first and second beads and positioning a fourth bead on the second cord longitudinally distal to the other of the first and second beads. The method also includes advancing a second band onto the endoscopic barrel to position the second band distally adjacent to the third and fourth beads.

The method can have various embodiments. For example, the method can include, after advancing the second band onto the ligation barrel, crossing the first and second cords at least once and then positioning a fifth bead on the first cord longitudinally distal to one of the third or fourth beads and positioning a sixth bead on the second cord longitudinally distal to the other of the third or fourth beads. The method can also include advancing a third band onto the endoscopic barrel to position the third band distally adjacent the fifth and sixth beads. In another example, crossing the first and second cords at least once includes twisting the first and second cords together at least once.

BRIEF DESCRIPTION OF THE DRAWINGS

The invention will be more fully understood from the following detailed description taken in conjunction with the accompanying drawings, in which.

DETAILED DESCRIPTION

Figure 1:
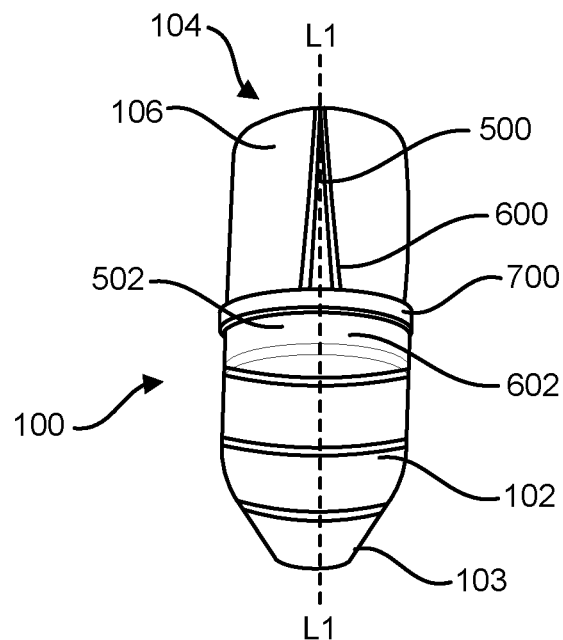
FIG. 1 is a side perspective view of one embodiment of a band ligation apparatus.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. The devices, methods, and systems discussed herein can be used with one or more of the devices, methods, and systems disclosed in U.S. Provisional Patent App. No. 62/085,272, International Patent App. No. WO 2016/086003, U.S. Patent Pub. No. 2017-0303930, U.S. Provisional Patent App. No. 62/622,345, and U.S. Design application. No. 29/635,038, all of which are incorporated herein by reference.

Devices, methods, and systems are provided herein for band ligation, including an approach to band deployment that provides consistent, effective band delivery. Consistent and even delivery of each ligation band to tissue is important to ensure tissue is cleanly grasped and ligated. Effective delivery can be achieved by ensuring that each ligation band is freed from the ligation barrel all at once, which can be difficult to accomplish when using two or more pull cords that extend parallel to each other along the exterior surface of the ligation barrel. A crisscrossed or engaged orientation between the pull cords along the exterior surface of the ligation barrel is thus provided to ensure consistent delivery of ligation bands to tissue and better visibility through the ligation barrel during use, resulting in better results for patients and an easier, safer operation for users.

FIGS. 1-12 illustrate one embodiment of a band ligation apparatus 100 for use with pull cords 500, 600 having a crisscrossed or engaged orientation. The band ligation apparatus 100 has a hollow elongate cylindrical barrel 102 with a proximal end 103 matable to an endoscope and/or configured to receive an imaging device therein, a distal end 104, and an inner lumen extending through the proximal and distal ends 103, 104. The proximal end 103 can be elastic for fitting over a distal end of an endoscope. The proximal end 103 can also include features to facilitate engagement of an endoscope, such as three elastic grooves or rings formed on an interior of the barrel 102 at the proximal end 103 that can stretch to mate with distal ends of imaging devices having cross-sectional areas of different sizes, as explained in more detail below. However, any mating feature can be used, such as ridges, threading, straps, etc.

Figure 2:
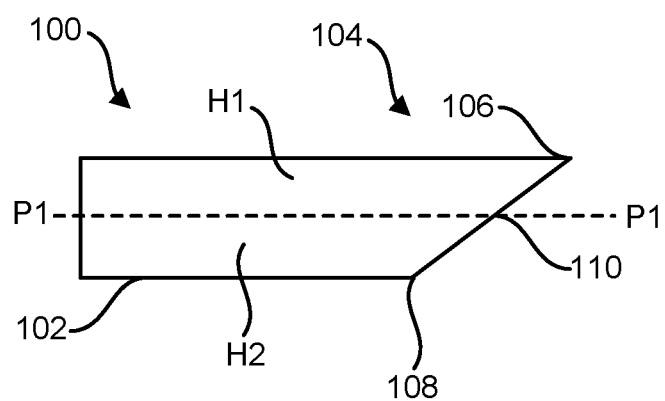
FIG. 2 is a line diagram of the band ligation apparatus of FIG. 1.

The distal end 104 can have a terminal end surface that extends at an oblique angle to a longitudinal axis L1 of the inner lumen. For reference purposes, the terminal end surface of the angled distal end 104 has a distal-most point 106 and a proximal-most point 108, for example as shown in FIG. 2. A horizontal plane P1 can extend along the axis L1 and through a mid-point 110 positioned equidistant between the distal-most point 106 and the proximal-most point 108, figuratively dividing the cylindrical barrel 102 into a first or high horizontal segment H1 and a second or low horizontal segment H2, as illustrated in FIG. 2.

Figure 8:
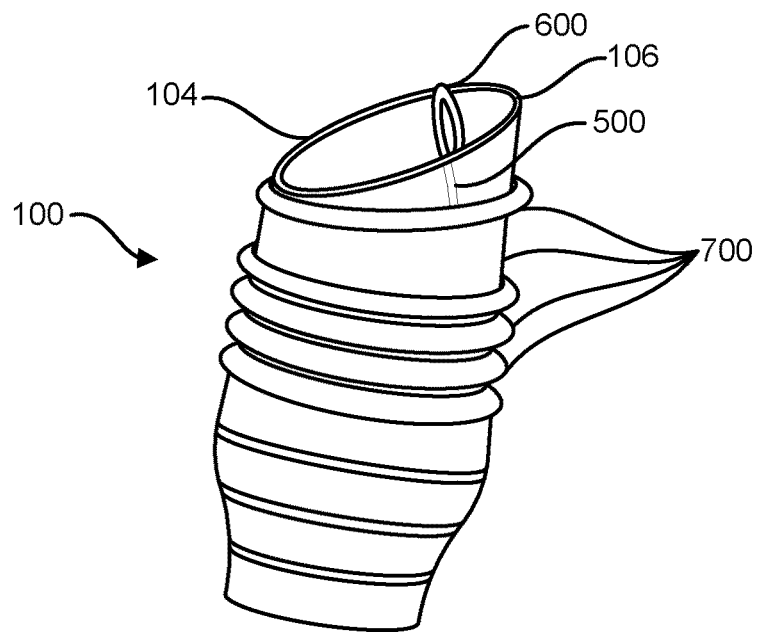
FIG. 8 is a side perspective view of the band ligation apparatus of FIG. 1.
Figure 9:
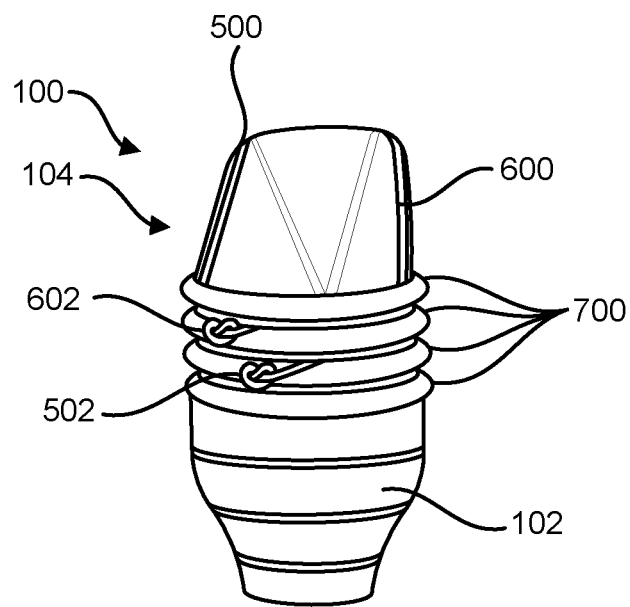
FIG. 9 is a side perspective view of the band ligation apparatus of FIG. 1.
Figure 10:
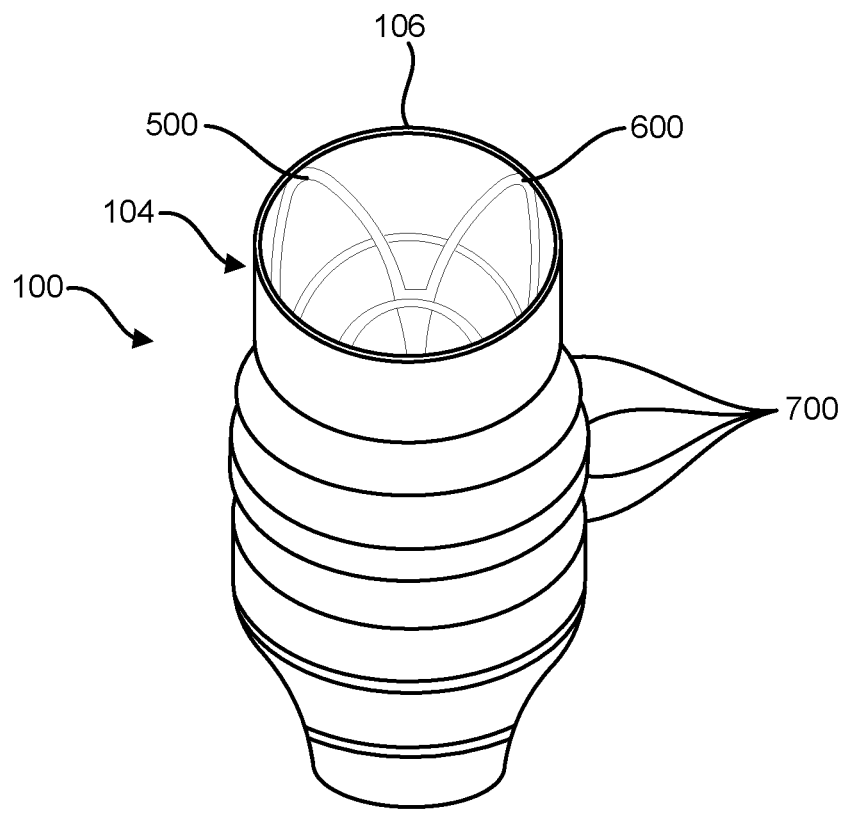
FIG. 10 is a side perspective view of the band ligation apparatus of FIG. 1.
Figure 11:
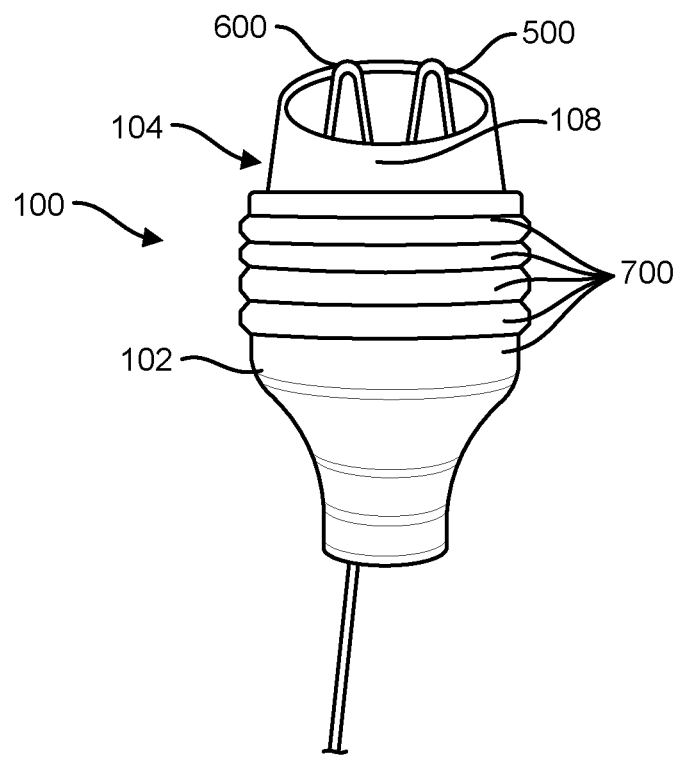
FIG. 11 is a side perspective view of the band ligation apparatus of FIG. 1.

The angled distal end 104 results in an opening with an ellipse or oval shape, for example as illustrated in FIGS. 8 and 10. The ellipse shape results in the distal end 104 having two diameters, a first being formed by a left-to-right or primary diameter that extends perpendicular to the longitudinal axis L1 and a second being formed by the distance from the distal-most point 106 to the proximal-most point 108. This second diameter can be extended in length by changing the angle of the terminal end surface of the distal end 104 relative to the axis L1. The angle can have a variety of ranges, for example from about 0 degrees to about 90 degrees, about 10 degrees to about 40 degrees, and more specifically about 20 degrees to about 30 degrees, such as around 29 degrees. In various embodiments, the area of tissue captured can be increased by changing the angle while leaving the primary diameter unchanged. For example, it is possible to increase the area of tissue capture by up to 50%. Extra length of the secondary diameter does not negatively affect maneuverability, such as when using intubation and/or when inserting into a lumen of a GI tract of a patient, while allowing greater tissue capture because the distal end 104 is angled forward and does not increase the primary diameter to maintain a smaller cross-sectional profile in the intubation tube. In some embodiments, the increased secondary diameter can be easier to intubate than a straight circular distal end when mated with the endoscope because of the projecting distal-most point 106, and it can be easier to make contact and begin creating a vacuum to suction tissue into the barrel. However, in other embodiments as further discussed below, a distal end of a band ligation apparatus can be approximately straight rather than angled, having a terminal end surface that extends at an approximately right or perpendicular angle to the longitudinal axis L1.

Two or more pull cords 500, 600 can each be configured to extend from a terminal trailing or distal end distally along the external surface of the barrel 102, loop around the distal end 104, and extend proximally through the inner lumen of the barrel. Terminal leading or proximal ends of each of the cords 500, 600, which extend proximally from the inner lumen of the barrel, can engage with a handle or other pull mechanism positioned proximal to the apparatus 100. As such, the cords 500, 600 can be pulled proximally through the inner lumen of the barrel 102, which can result in pulling terminal distal ends of the cords 500, 600 (located against the external surface of the barrel 102) distally along the external surface of the apparatus 100. Each of the cords 500, 600 are subsequently pulled around the distal end 104 and pulled entirely within the inner lumen of the barrel 102 to continue to move proximally through the barrel 102. Beads or knots 502, 602 can be spaced axially and immovably fixed along at least a distal portion of each cord 500, 600, and the beads 502, 602 can be configured to engage with ligation bands 700. One or more ligation bands 700 can be configured to wrap around the outer surface of the apparatus 100 on a distal portion thereof. The bands 700 can be pushed distally by retraction of the cords 500, 600 and corresponding distal movement of the beads 502, 602 such that each band 700 is deployed sequentially off the distal end 104 of the apparatus 100 when each corresponding bead 502, 602 loops over the distal end 104 and is pulled into the barrel 102.

Spacing of the beads 502, 602 and lengths of the cords 500, 600 can be varied such that proximal movement of proximal terminal ends of the cords 500, 600 will result in deployment of ligation bands 700 at known distances. For example, spacing between an initial bead 502, 602 at the distal terminal end of each of the cords 500, 600 and a second subsequent bead 502, 602 can be longer than the spacing between the second subsequent bead 502, 602 and a third subsequent bead 502, 602. Therefore, the initial bead 502, 602 can be loaded first on the apparatus 100 with a corresponding band 700 and will thus be last to cause deployment of the band 700. The spacing length can consequently be longer to accommodate the longer distance required to move the last band 700 distally to deploy. However, the spacing of the beads can also be equidistant in some embodiments.

During loading of the bands 700 onto the band ligation apparatus 100, the cords 500, 600 can be engaged with or crisscross each other between each band 700 to allow an even, consistent deployment of the bands 700. Each band 700 can be deployed from the angled distal end 104 all at once, avoiding one side of the band 700 (on the side of the low horizontal segment H2) from being deployed before a second side of the band 700 (on the side of the high horizontal segment H1). If parts of the band 700 come free from the distal end 104 before others, delivery of the band 700 can be uneven. Furthermore, by engaging or crisscrossing the cords 500, 600, the pull cords 500, 600 are prevented from slipping or sliding to the low horizontal segment H2, which would cause uneven advancement of the bands and an uneven delivery.

Figure 3:
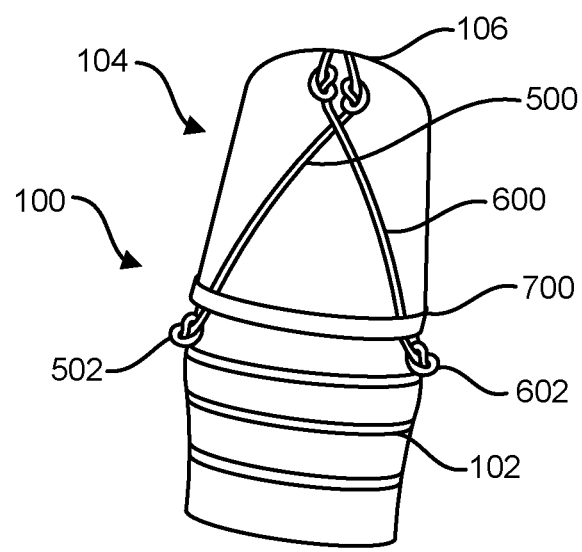
FIG. 3 is a side perspective view of the band ligation apparatus of FIG. 1.
Figure 4:
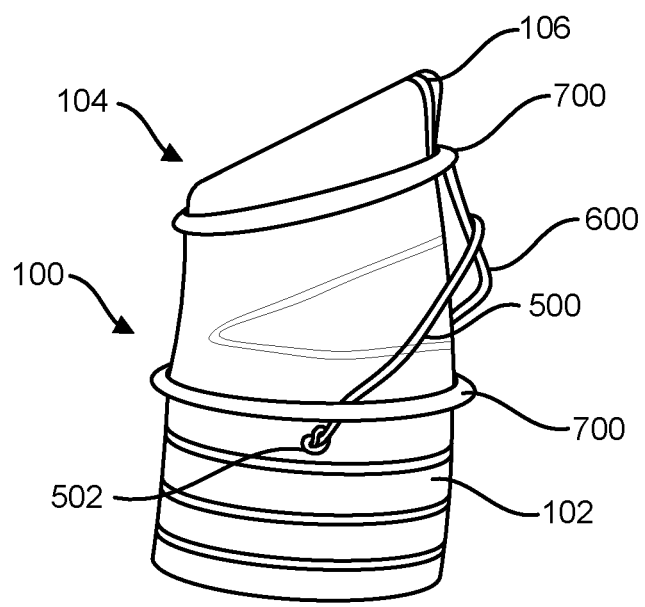
FIG. 4 is a side perspective view of the band ligation apparatus of FIG. 1.
Figure 5:
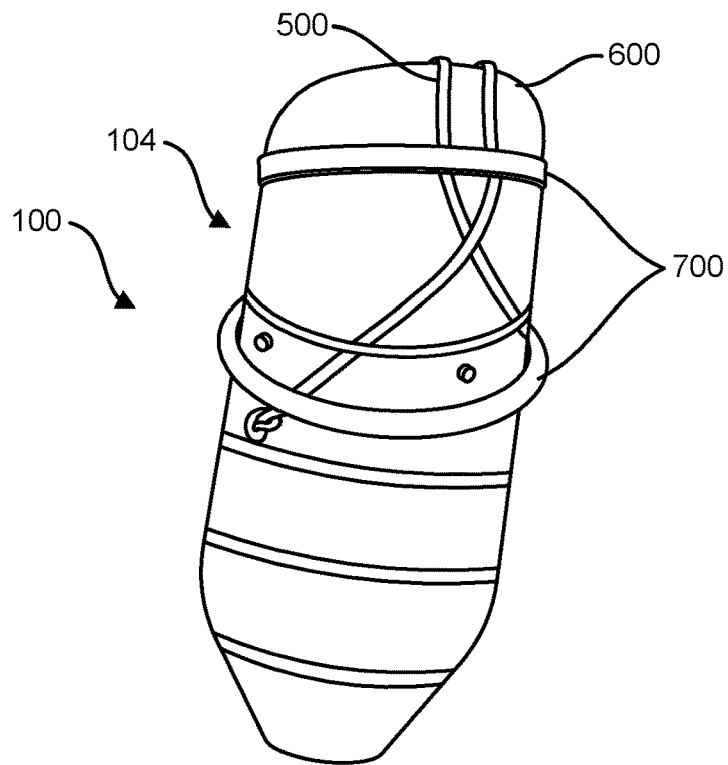
FIG. 5 is a side perspective view of the band ligation apparatus of FIG. 1.
Figure 6:
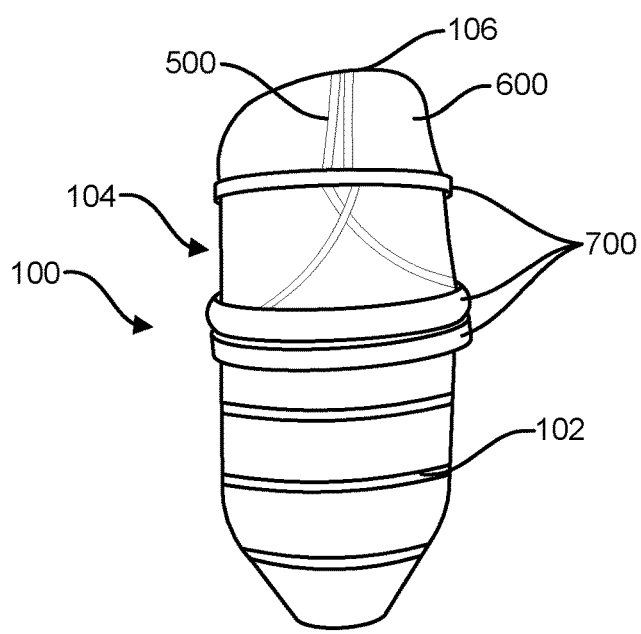
FIG. 6 is a side perspective view of the band ligation apparatus of FIG. 1.
Figure 7:
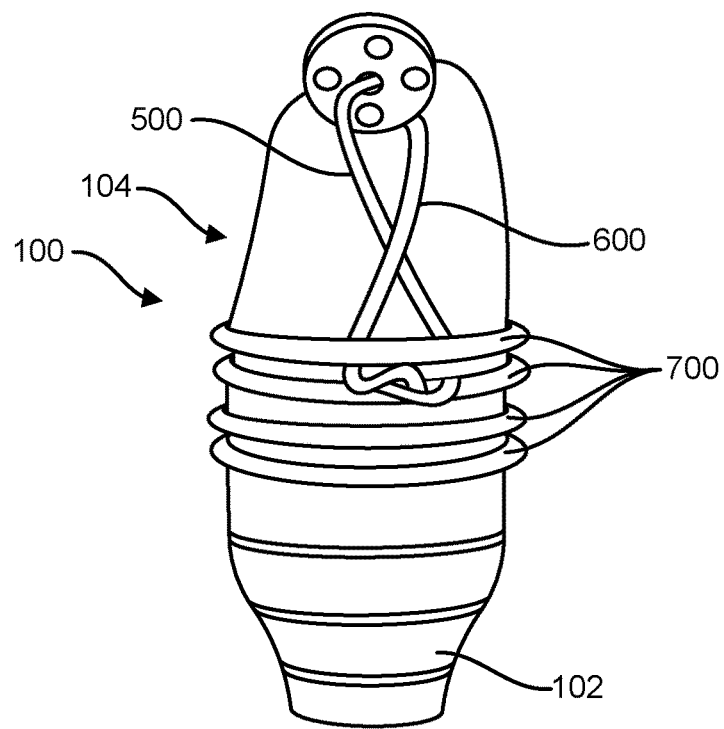
FIG. 7 is a side perspective view of the band ligation apparatus of FIG. 1.

As illustrated in FIG. 1, beads 502, 602 on the distal terminal ends of the cords 500, 600 can be aligned on the outer surface of the apparatus 100 proximal to where the first band 700 to be loaded (and thus the last band 700 to be deployed) will be placed. The first beads 502, 602 can be positioned on the same side as the high horizontal segment H1 of the cylindrical barrel 102 to help ensure that the band 700 will be deployed correctly. For example, assuming the opening of the distal end 104 of the apparatus 100 represents a clock with the distal-most point 106 at 12 o'clock, the first beads 502, 602 can be positioned between 9 o'clock and 3 o'clock, for example at 10 o'clock and 2 o'clock or 11 o'clock and 1 o'clock, or somewhere therebetween. With the beads positioned on the high horizontal segment H1 and the cords extending along the exterior surface of the barrel 102, a first band 700 can be advanced over the cords 500, 600 to position the first band 700 on the barrel 102 at a location immediately distal of the beads 502, 602. In certain embodiments, after the first set of beads 502, 602 and the first band 700 are loaded, the cords 500, 600 can be engaged with each other, for example by being crisscrossed as illustrated in FIG. 3. By crisscrossing the cords 500, 600 between each band, the beads 502, 602 will remain on the high horizontal segment H1 as they are pulled behind their corresponding band 700, and the beads 502, 602 will move toward the distal-most point 106 (corresponding to 12 o'clock along the high horizontal segment H1 of the barrel 102). In various embodiments, the cords 500, 600 can be crossed once or can be looped or twisted around each other one or more times. The second set of beads 502, 602 and the second band 700 can then be loaded over the cords 500, 600 to position the second band 700 immediately distal of the second set of beads 502, 602, as illustrated in FIGS. 4-6. The second band 700 to be loaded will be the second-to-last band 700 to be fired, and the band 700 can optionally be a different color from the remaining bands to indicate its position to a user during deployment. The process can be repeated to load the remaining bands, as illustrated in FIGS. 7-11.

Figure 12:
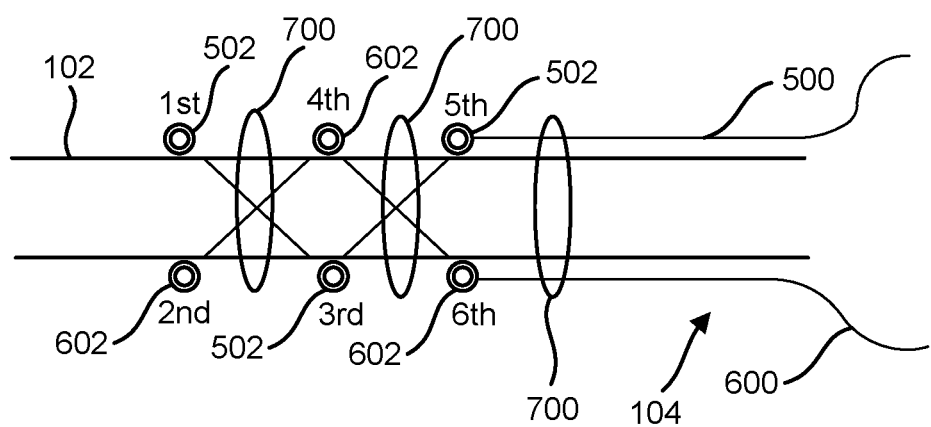
FIG. 12 is a line diagram of the band ligation apparatus of FIG. 1.

During loading, each set of beads 502, 602 can move radially outward away from the 12 o'clock position along the outer surface of the apparatus 100 as each band 700 is pushed toward the previously-loaded band 700 until the beads 502, 602 are tight and lined up with any previously-loaded beads 502, 602. FIG. 12 illustrates a simplified diagram with sets of beads 502, 602 and corresponding bands 700 labeled to indicate a possible order of loading and to illustrate the crisscrossing of the cords 500, 600 between each set of beads 502, 602 and corresponding band 700. While the cords 500, 600 are crossed once in FIG. 12, the cords can be twisted one or more times. If the cords 500, 600 are crossed and twisted an odd number of times, the beads 502, 602 will align with beads 502, 602 from the same cord 500, 600. If the cords are crossed and twisted an even number of times, the beads 506, 602 will align with beads 502, 602 from the other cord 500, 600. While crisscrossing or engaging the cords 500, 600 is discussed with reference to the angled distal end 104, a similar approach can be used on a straight distal end, as discussed below. On such a straight distal end, each point of crisscrossing or engagement between the cords 500, 600 can be positioned on a same side of the exterior surface of the barrel every time, as illustrated above with reference to the apparatus 100 having an angled distal end 104, or can be positioned on an opposite side for some of the points of crisscrossing or engagement.

A plurality of bands and beads can be loaded until a user is satisfied, for example 10 ligation bands or more. The proximal terminal ends of the cords 500, 600 can be looped around the distal end 104 of the band ligation apparatus 100 and can be extended proximally through the barrel 102 and optionally through an endoscope. The cords 500, 600 can optionally be knotted together within the barrel 102 or proximal to the barrel 102 to ensure that the cords 500, 600 are pulled evenly together during later deployment. The cords 500, 600 can also optionally be engaged with various handles and/or pulling mechanisms (for example on a proximal end of an endoscope) for use during later deployment.

Figure 13:
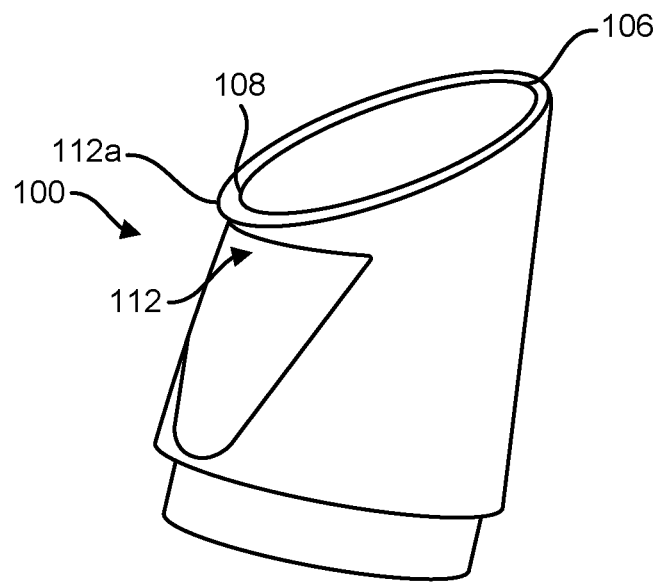
FIG. 13 is a side perspective view of the band ligation apparatus of FIG. 1.
Figure 14:
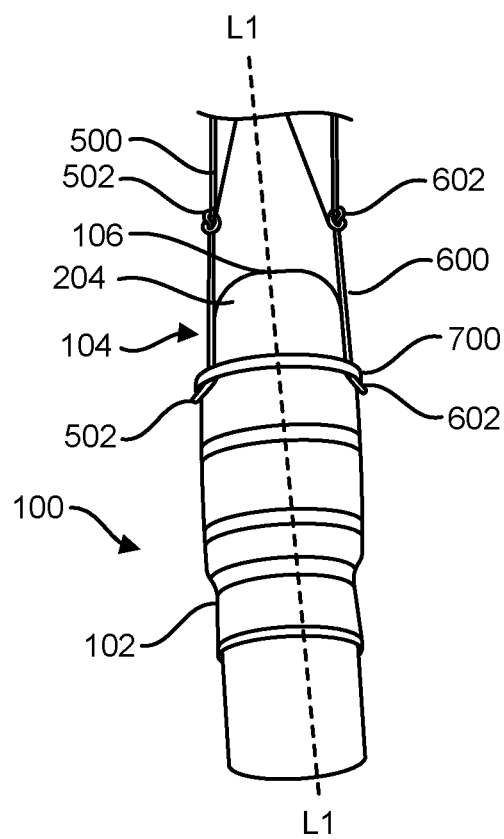
FIG. 14 is a side perspective view of one embodiment of a loading apparatus engaged with the band ligation apparatus of FIG. 1.

In some embodiments, an optional notch 112 can be formed close to the proximal-most point 108 of the terminal end surface along the distal end 104 on the low horizontal segment H2, as illustrated in FIG. 13. The notch 112 can engage each ligation band 700 during deployment to help ensure even deployment (as explained below). The notch 112 as illustrated is formed by a distally-inward sloped outer surface on the low horizontal segment H2 that terminates proximal of the terminal distal end, thereby defining a rim 112*a* distally adjacent the notch 112. Such a configuration allows the bands 700 to easily slide proximally onto the outer surface of the apparatus 100 during loading, while still allowing the notch 112 to be effective to engage the bands 700 during deployment (as explained below). In certain exemplary embodiments, the sloped surface can have between approximately 1 and 20 degrees of slope, and more specifically between approximately 5 and 10 degrees, such as 8 degrees of slope. In other embodiments, the notch can be in the form of a groove, channel, bump, hook, engagement feature, etc. While a notch is illustrated herein, ligation barrels using a crisscrossing or engaging pull cord orientation are possible that do not include notches.

Figure 15:
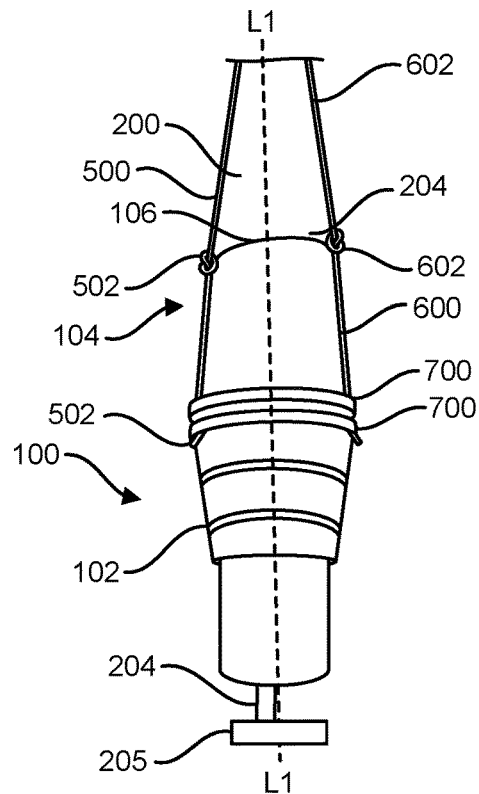
FIG. 15 is a side perspective view of the loading apparatus of FIG. 14 engaged with the band ligation apparatus of FIG. 1.
Figure 16:
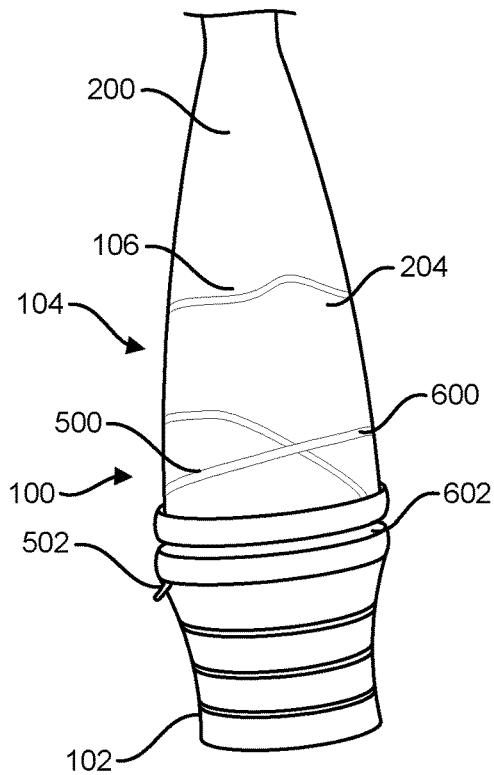
FIG. 16 is a side perspective view of the loading apparatus of FIG. 14 engaged with the band ligation apparatus of FIG. 1.
Figure 17:
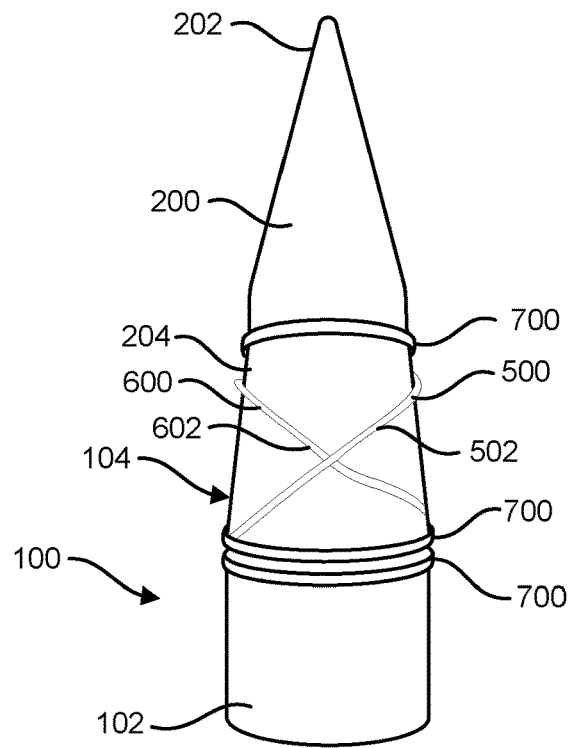
FIG. 17 is a side perspective view of the loading apparatus of FIG. 14 engaged with the band ligation apparatus of FIG. 1.
Figure 18:
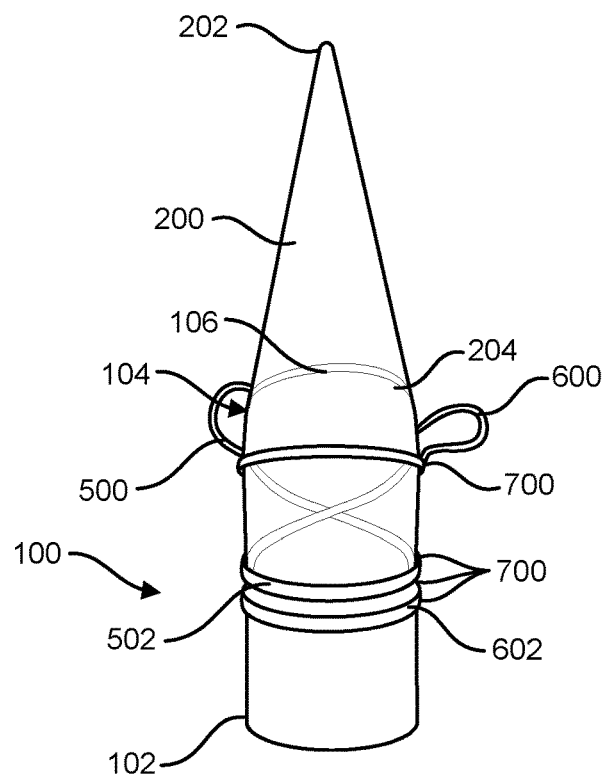
FIG. 18 is a side perspective view of the loading apparatus of FIG. 14 engaged with the band ligation apparatus of FIG. 1.
Figure 19:
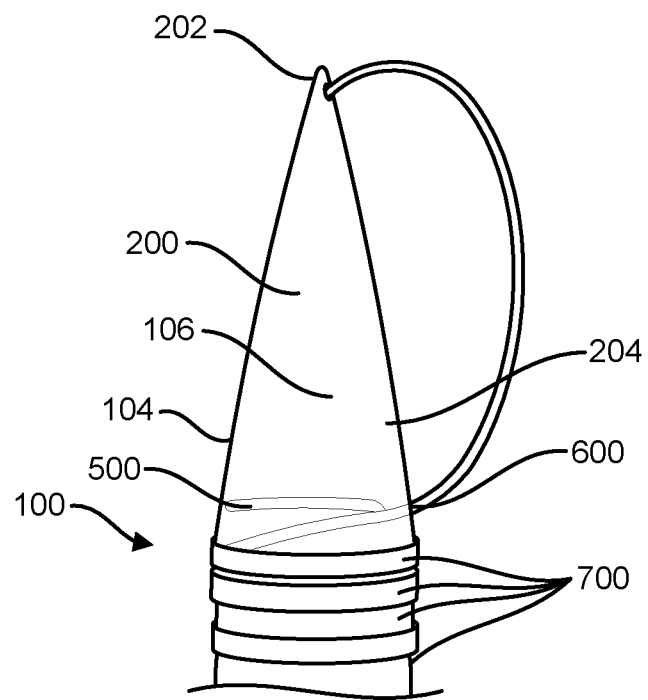
FIG. 19 is a side perspective view of the loading apparatus of FIG. 14 engaged with the band ligation apparatus of FIG. 1.
Figure 20:
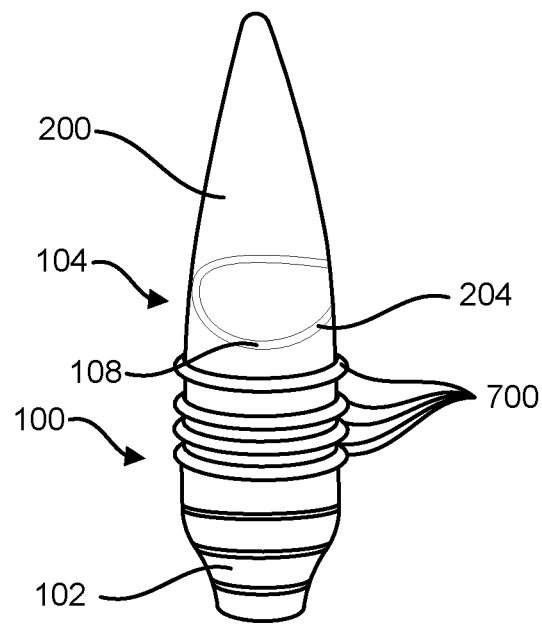
FIG. 20 is a side perspective view of the loading apparatus of FIG. 14 engaged with the band ligation apparatus of FIG. 1.

A loading apparatus 200 can also optionally be used to assist a user in loading one or more ligation bands 700 onto the band ligation apparatus 100, as illustrated in FIGS. 14-20. The illustrated loading apparatus 200 includes a rigid cone with a distal-most point 202 that increases in diameter radially in a proximal direction until it reaches an engagement edge or groove 204 that fits flush with the distal end 104 of the band ligation apparatus 100. The engagement edge 204 has a diameter and shape corresponding to the diameter and shape of the distal end 104 of the apparatus 100 such that the loading apparatus 200 can be securely fit into the oval shape of the distal end 104. The loading apparatus 200 is oblique to ensure the loading apparatus 200 can only engage the band ligation apparatus 100 in one, correct orientation. However, other orientations are possible to accommodate distal ends having different angles, for example straight distal ends. The cone-shape of the loading apparatus 200 can dilate ligation bands 700 such that the bands 700 are able to stretch and slide onto the barrel 102 for eventual deployment. A shaft 204 extending proximally from the engagement edge 204 fits along the hollow elongate cylindrical barrel 102 and extends proximally therefrom, as illustrated in FIG. 15. In some embodiments, at least a proximal section of the shaft 204 can be threaded to receive a nut 205 therearound. The nut 205 can be rotated around the threaded portion of the shaft 204 to bring the nut 205 into secure engagement with the proximal end 103 of the apparatus 100 such that the engagement edge 204 of the loading apparatus 200 is secured into the distal end 104 of the apparatus 100 for loading. In certain embodiments, an outer surface of the loading apparatus 200 can have marks on it to indicate proper alignment of cords 500, 600 and bands 700 during loading. For example, the marks can indicate preferred loading alignments on the high horizontal segment H1 of the cylindrical barrel 102.

During use, the band ligation apparatus 100 can mate or engage with a variety of different imaging devices and/or endoscopes. An exemplary endoscope can have illumination and viewing apparatus(es) to facilitate orientation within the body of a patient, longitudinally extending tubular passages such as one or more channels through which objects may be passed and suction applied for drawing tissue into the distal end 104 of the apparatus 100 to facilitate ligation of a lesion, and a working channel through which one or more flexible actuating cables can be inserted.

Once the apparatus 100 is inserted into a patient, suction can be applied to the endoscope to draw tissue to be ligated into the distal end 104 of the hollow barrel 102 of the band ligation apparatus 100. A user can retract the cords 500, 600 proximally, which will cause the set of beads 502, 602 positioned distal-most on the outer surface of the apparatus 100 to begin to move distally along the outer surface. As noted above, the crisscrossed pattern of the cords 500, 600 will cause each bead 502, 602 to move toward the distal-most point 106 (corresponding to 12 o'clock along the high horizontal segment H1 of the cylindrical barrel 102) as the beads 502, 602 are moved distally and push their corresponding band 700 distally. The beads 502, 602 will be crisscrossed and equidistant from a center of the high horizontal segment H1. Thus each set of beads 502, 602 will deploy their corresponding band 700 evenly despite the angled distal end 104 because they will be drawn toward the distal-most point 106. Because the cords 500, 600 are both loaded on a same side of the barrel 102 (the high horizontal segment H1), they can be retracted proximally through the barrel 102 on a same side and thus can allow for increased visibility through the barrel 102.

If the notch 112 is formed on the apparatus 100, the notch 112 engages each band 700 as it is drawn distally for deployment. The notch 112 acts to delay firing of each band 700 on the side of the low horizontal segment H2 until the band 700 has reached the distal end 104 on the side of the high horizontal segment H1. Thus, the band 700 is released either simultaneously all around or is released on the side of the high horizontal segment H1 first. The delayed release on the side of the low horizontal segment H2 can help prevent the band 700 from deploying unevenly and potentially firing straight across the distal end 104 of the apparatus 100 instead of capturing tissue therein.

Figure 21:
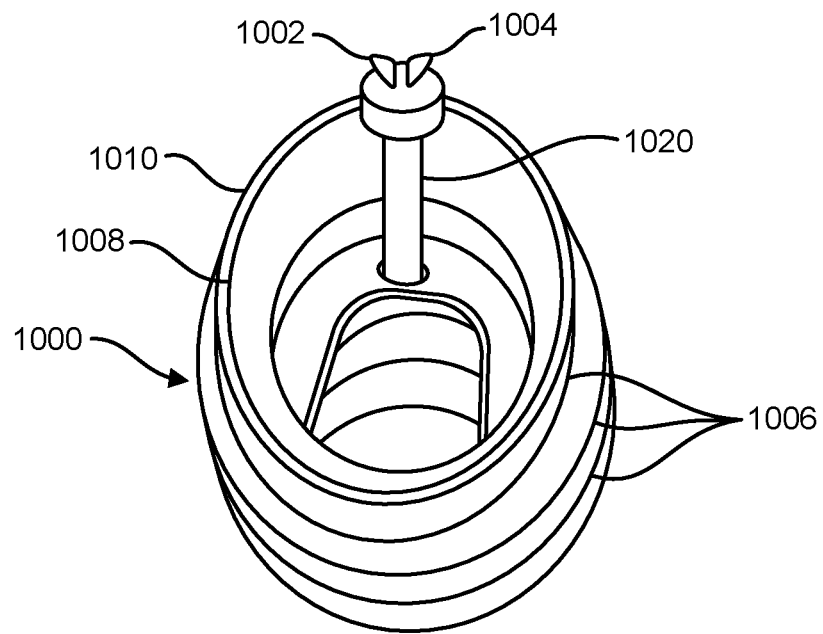
FIG. 21 is a top perspective view of a distal end of another embodiment of a band ligation apparatus.

The band ligation apparatus can have a variety of alignment features formed thereon to provide assistance to users in keeping cords aligned during use, thus helping to ensure even, consistent delivery of ligation bands. FIG. 21 illustrates a band ligation apparatus 1000 that generally corresponds to apparatus 100 and has pull cords 1002, 1004, ligation bands 1006, and a hollow elongate cylindrical barrel 1008. In this embodiment, the barrel 1008 has a cord alignment feature, represented here by a tube 1020, extending along an inner surface of the barrel 1008 and running parallel to a longitudinal axis of the barrel 1008. The tube 1020 is positioned at least along a distal portion of the barrel 1008 such that its distal terminal end is positioned close to a distal end 1010 of the barrel 1008. The tube 1020 is also approximately aligned with a distal-most point of the distal end 1010 of the barrel 1008, corresponding generally to 12 o'clock (as discussed above in apparatus 100). The tube 1020 can be configured to receive the cords 1002, 1004 therethrough. As such, when the cords 1002, 1004 are pulled proximally to deploy the ligation bands 1006, the cords 1002, 1004 are maintained in proper alignment to ensure even deployment, for example by maintaining the cords 1002, 1004 within a range of between approximately 9 o'clock and 3 o'clock.

Figure 22:
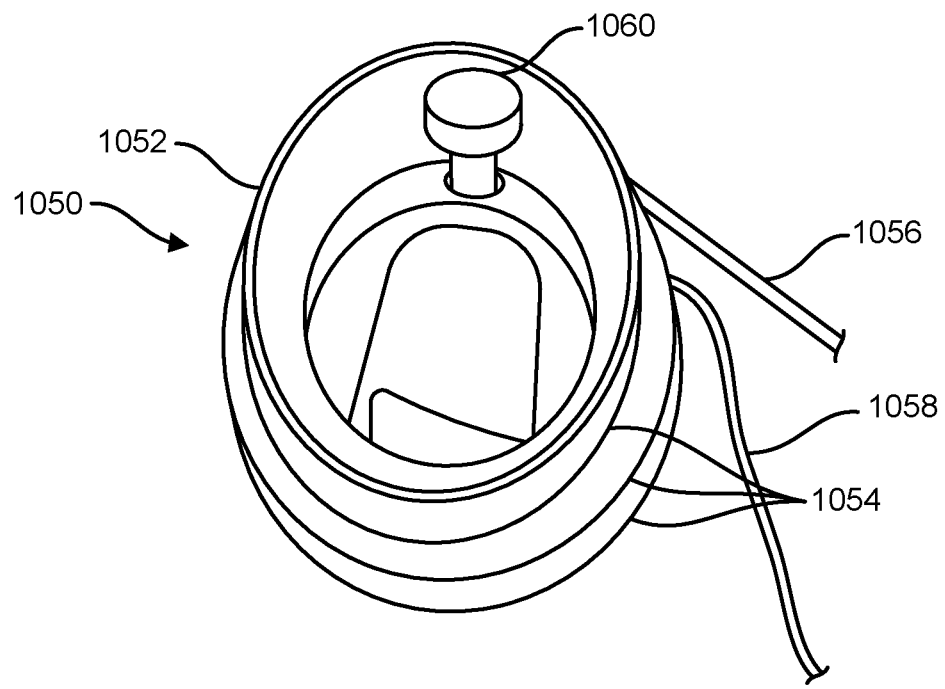
FIG. 22 is a top perspective view of a distal end another embodiment of a band ligation apparatus.

While a tube 1020 is illustrated in FIG. 21, a variety of different alignment features can be used, such as rings, hooks, loops, burr holes, grooves, channels, etc. For example, FIG. 22 illustrates a band ligation apparatus 1050 with a barrel 1052, bands 1054, and cords 1056, 1058 similar to apparatus 100. However, it has a ring 1060 positioned at approximately the same point as the tube 1020 and configured to align the cords 1056, 1058 during actuation.

The alignment features can allow the cords to come close together at the distal-most point of the band ligation apparatus to help ensure one central pulling force on the cords. If a loading apparatus is used, the corresponding loading apparatus can also have a corresponding channel or groove thereon to receive the alignment feature so that the loading device has an outer surface that is shaped to complement the shape of the inner lumen of the barrel to achieve a flush fit.

Figure 23:
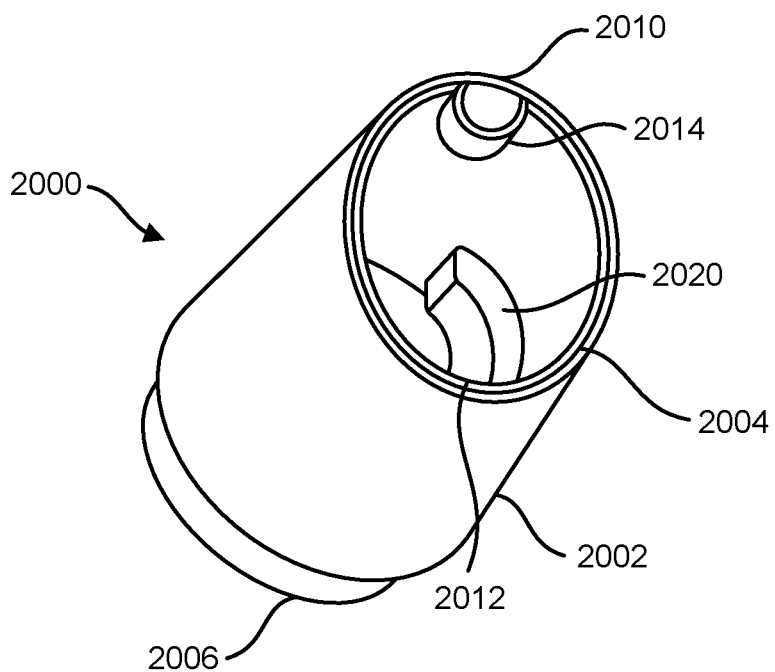
FIG. 23 is a side perspective view of another embodiment of a band ligation apparatus.
Figure 24:
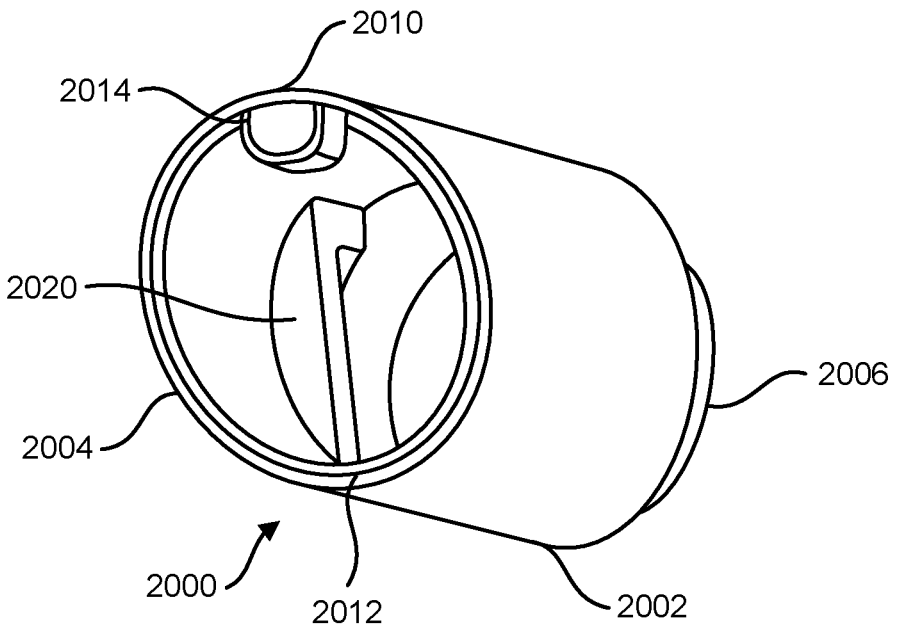
FIG. 24 is a side perspective view of the band ligation apparatus of FIG. 23.

Additional features can be provided to assist in suctioning tissue to a certain depth within the ligation barrel. FIGS. 23 and 24 illustrate another embodiment of a band ligation apparatus 2000 that is similar to apparatus 100 and has a hollow elongate cylindrical barrel 2002 with distal and proximal ends 2004, 2006. The distal end 2004 is angled similar to apparatus 100, and it has a distal-most point 2010 and a proximal-most point 2012 located on the terminal end surface. A hoop 2014 is generally aligned with the distal-most point 2010 and acts to align pull cords during use. The hollow barrel 2002 has a tissue-stopping feature, represented here by a ledge 2020, that is positioned within and formed on an inner surface of the barrel 2002. The ledge 2020 can extend at least partially around the circumference of the inner surface of the barrel 2002, and as can be seen in FIGS. 23 and 24, can include two or more separate ledges protruding inwardly from opposite sides of the inner surface. The ledge 2020 can be configured to allow the cords to extend therethrough while stopping tissue from being retracted too far into the barrel 2002. The ledge 2020 can have an angle that is the same as the angle of the distal end 2004 of the apparatus 2000. For example, the angle of the ledge 2020 and the distal end 2004 can be 29 degrees (with the distal-most point 2010 located at 29 degrees and the proximal-most point 2012 located at 0 degrees). However, the angle can be varied as explained above from approximately 0 degrees to approximately 90 degrees.

In certain exemplary embodiments, the depth of the ledge 2020 can be approximately 7 mm to prevent tissue from being drawn into the barrel 2002 any deeper than 7 mm. Because the ledge 2020 is angled similarly to the distal end 2004, the depth of the ledge 2020 represents the distance from the distal end 2004 all around. 7 mm is approximately the depth used to draw in tissue without drawing in any muscle. However, a variety of different depths can be used depending on the desired use. Without the ledge 2020, tissue can potentially be drawn into the barrel 2002 until it hits the corresponding scope, and when tissue is ligated, the tissue on the high side will be deeper. This can potentially leave an uneven ligation in the shape of a wedge. The ledge 2020 is thus configured to allow suction and maintain visualization for the user while also ensuring that acceptable amounts of tissue are ligated. While ledges are illustrated, a variety of different protuberances can be used, such as tabs, bumps, cylinders, etc. While a depth of approximately 7 mm is provided, any depth can be used. For example, a depth can range from approximately 4 mm to approximately 12 mm, or approximately 4 mm, 5 mm, 6 mm, 7 mm, 8 mm, 9 mm, 10 mm, 11 mm, 12 mm, etc.

Figure 25:
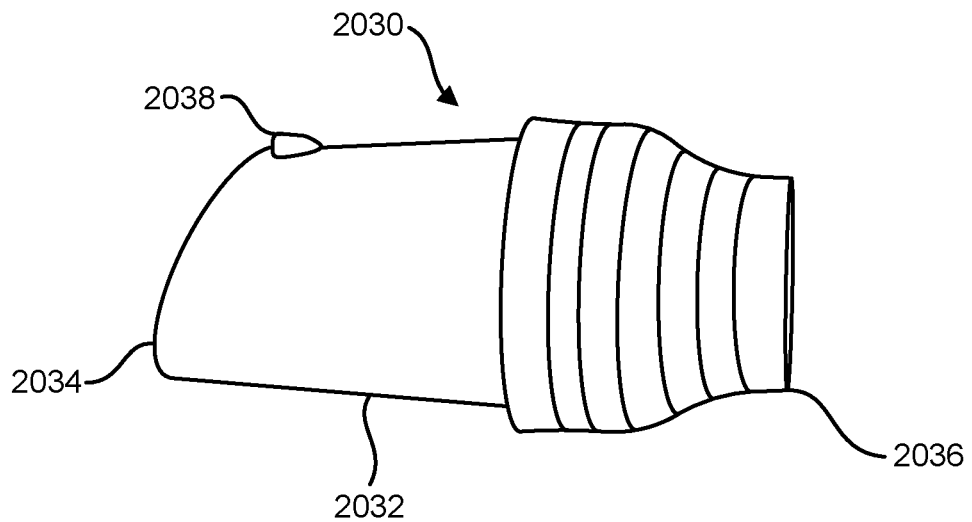
FIG. 25 is a side perspective view of another embodiment of a band ligation apparatus.
Figure 26:
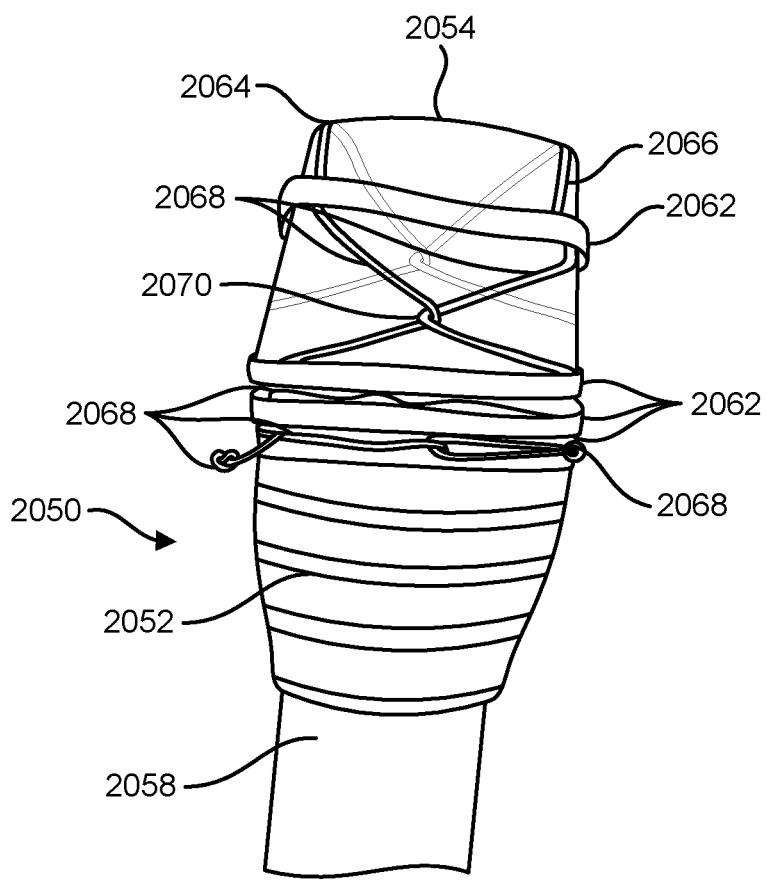
FIG. 26 is a side perspective view of another embodiment of a band ligation apparatus.
Figure 27:
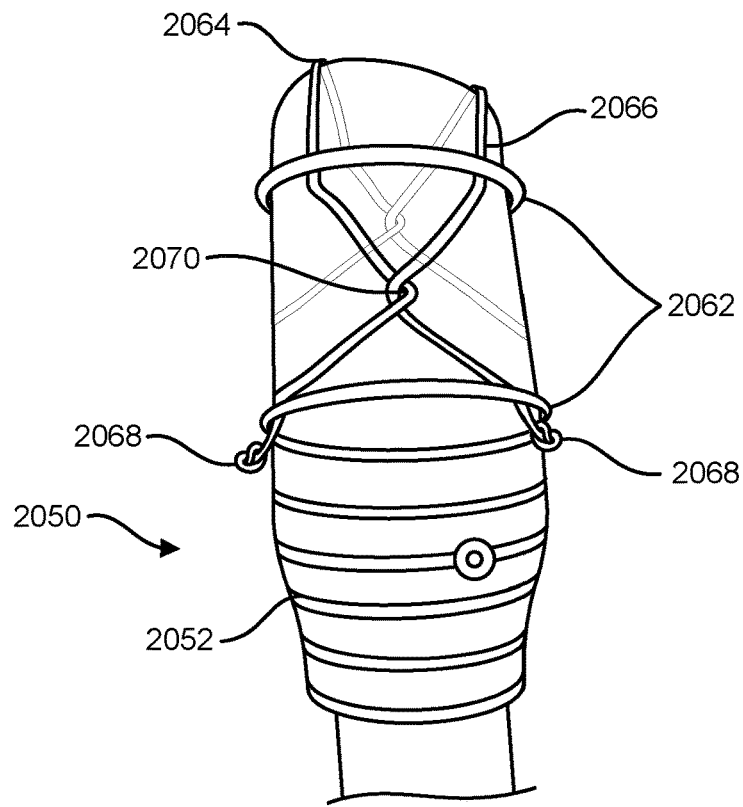
FIG. 27 is a side perspective view of the band ligation apparatus of FIG. 26.
Figure 28:
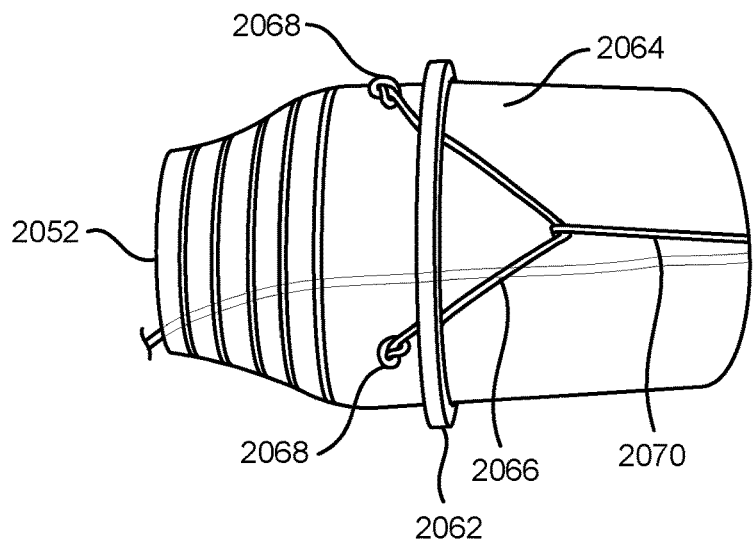
FIG. 28 is a side perspective view of the band ligation apparatus of FIG. 26.
Figure 29:
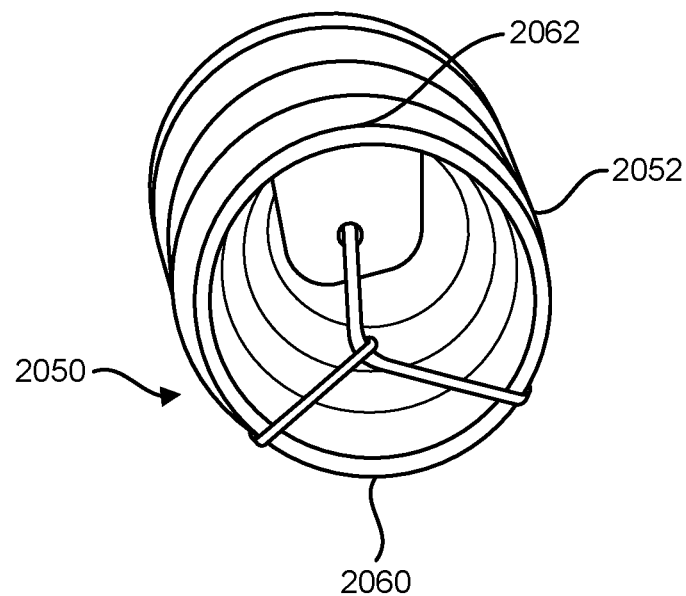
FIG. 29 is a distal-to-proximal end perspective view of the band ligation apparatus of FIG. 26.
Figure 30:
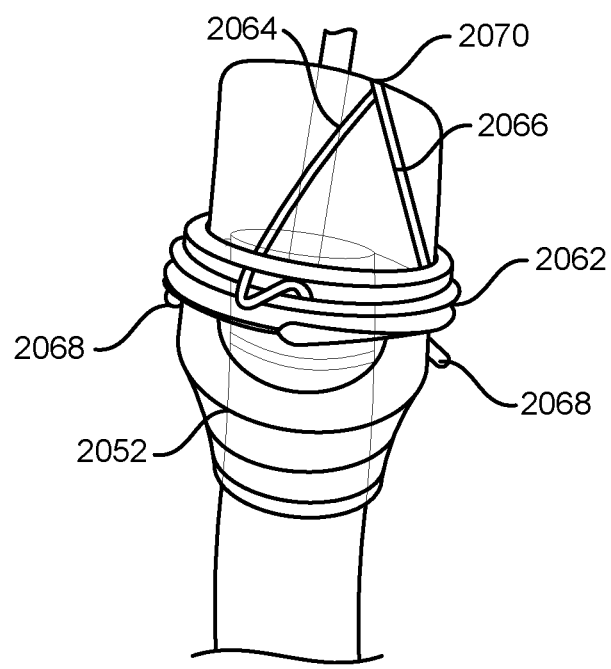
FIG. 30 is a side perspective view of the band ligation apparatus of FIG. 26.
Figure 31:
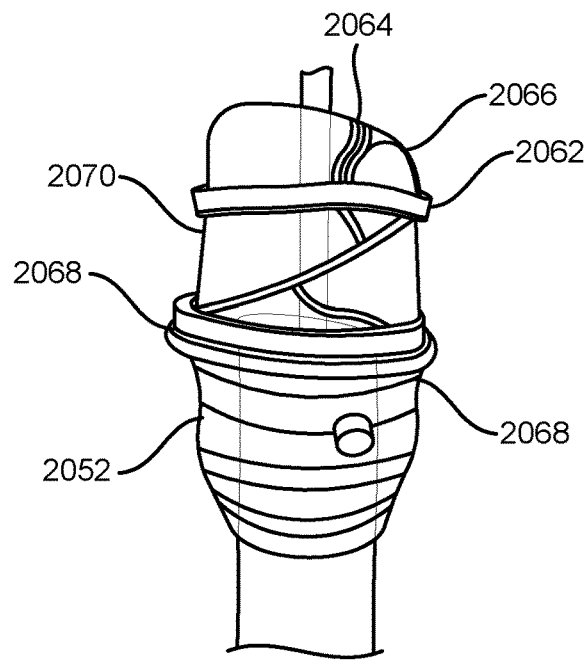
FIG. 31 is a side perspective view of the band ligation apparatus of FIG. 26.
Figure 32:
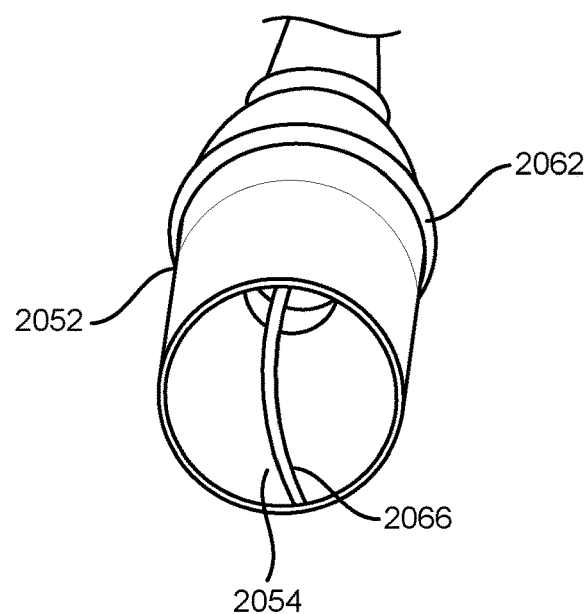
FIG. 32 is a distal-to-proximal end perspective view of the band ligation apparatus of FIG. 26.
Figure 33:
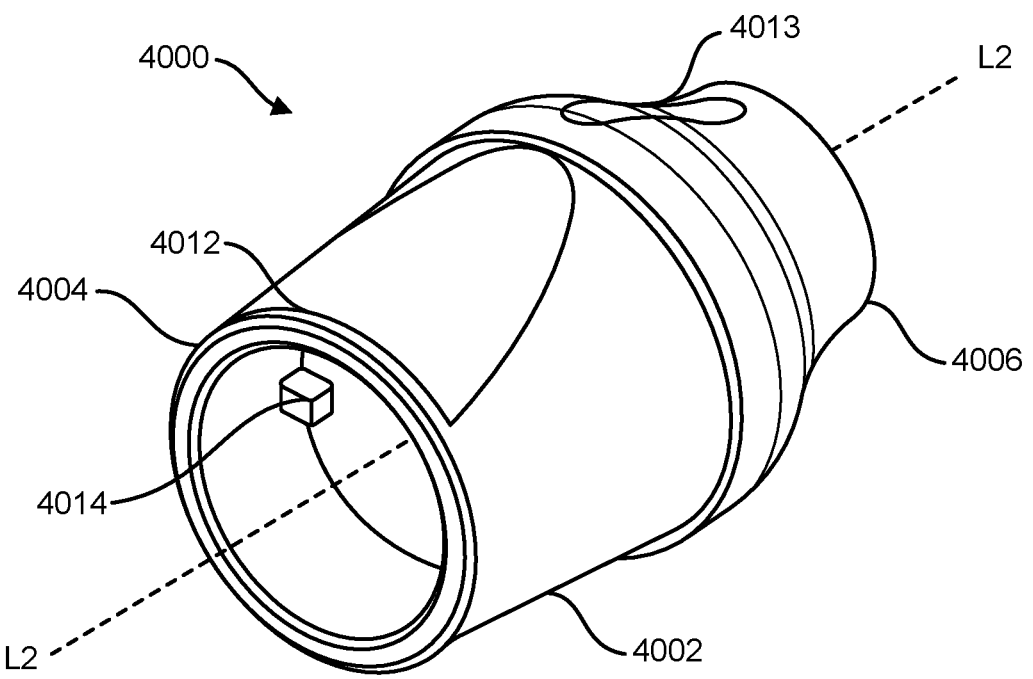
FIG. 33 is a side perspective view of another embodiment of a band ligation apparatus.
Figure 34:
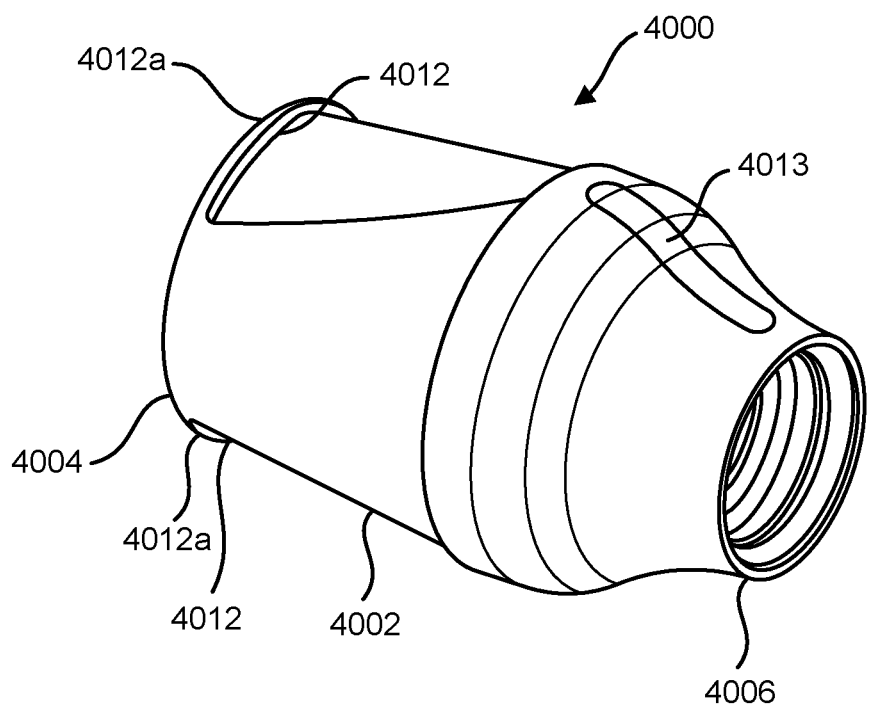
FIG. 34 is a side perspective view of the band ligation apparatus of FIG. 33.
Figure 35:
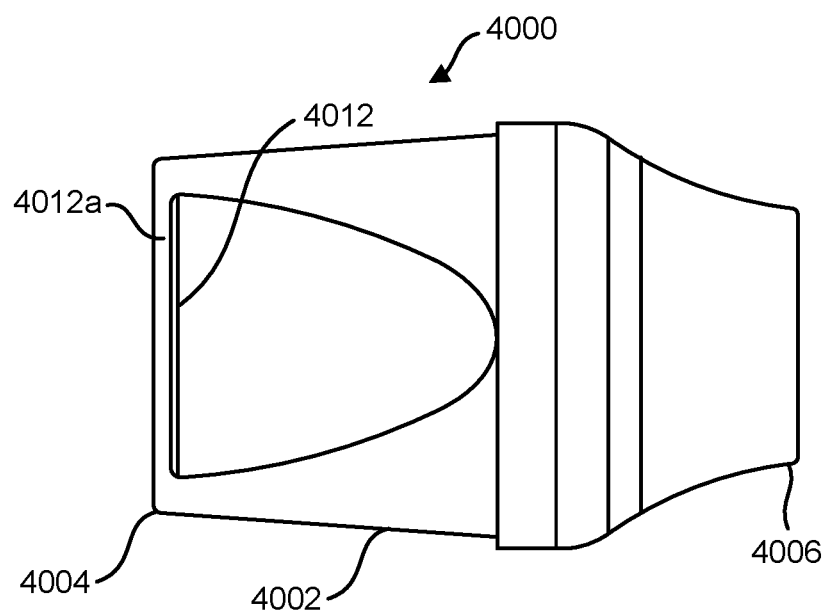
FIG. 35 is a side view of the band ligation apparatus of FIG. 33.

A variety of different elements can also be used for ligation band delay similar to notch 112. FIG. 25 illustrates another embodiment of a band ligation apparatus 2030 that is similar to the apparatus 100 and has a hollow elongate cylindrical barrel 2032 with distal and proximal ends 2034, 2036. The distal end 2034 is angled similar to apparatus 100. However, the apparatus 2030 has a bump 2038 that functions similar to notch 112. The bump 2038 can be formed close to a proximal-most point of the distal end 2034 and can be configured to engage and delay each ligation band during deployment (as explained above).

One or more pull cords of different lengths and having different placements of beads can also be used on a ligation barrel. FIGS. 26-32 illustrate another embodiment of a band ligation apparatus 2050 that is similar to apparatus 100 and that has a hollow elongate cylindrical barrel 2052 with distal and proximal ends 2054, 2056. The apparatus 2050 is configured to be disposed on a distal end of an endoscope 2058, and the distal end 2054 is angled similar to apparatus 100 such that, for reference purposes, it has a distal-most point 2060 and a proximal-most point 2062. Bands 2062 and cords 2064, 2066 with beads 2068 are disposed thereon. However, unlike beads 502, 602 disposed on cords 500, 600 at varying distances, the beads 2068 are disposed on at least one of the cords 2064, 2066 at regular intervals (i.e., equidistant from one another) along at least distal portions thereof. Because the bands 2062 may need to travel different distances along the outer surface of the barrel 2052 to be deployed based on their loading order, the cords 2064, 2066 can be twisted one or more times to form twisted points 2070 between subsequent bands 2062 to prevent excess cord from accidentally causing a jam or double deployment. The one or more twists in the cords 2064, 2066 are thus configured to reduce slack in the cords 2064, 2066. The number of twists per twisted point 2070 can vary depending on the length of the cords and the position of the beads. For example, four twists can be used for a first twisted point 2070, three for a second, etc., to make cords into the desired lengths so that tension is applied to the bands at proper times. The twisted points 2070 can also assist in keeping beads 2068 between a 9 o'clock and a 3 o'clock range (assuming 12 o'clock corresponds to the distal-most point 2060). Because one or more twists can be used in the cords, beads can have a variety of arrangements in other embodiments. For example, all beads 2068 for one cord 2062 can align with each other while all beads 2068 for the other cord 2064 can align with each other (depending on the number of twists in the cords).

While the ligation barrels above have angled distal ends, ligation barrels with straight distal ends can benefit from use of a crisscrossing or engaging orientation of pull cords, as well. FIGS. 33-37 illustrate another embodiment of a band ligation apparatus 4000 that is similar to apparatus 100. The apparatus 4000 has a hollow elongate cylindrical barrel 4002 with distal and proximal ends 4004, 4006. The distal end 4004 is straight, however, being formed at a right or perpendicular angle to a longitudinal axis L2 of the barrel 4002.

Figure 36:
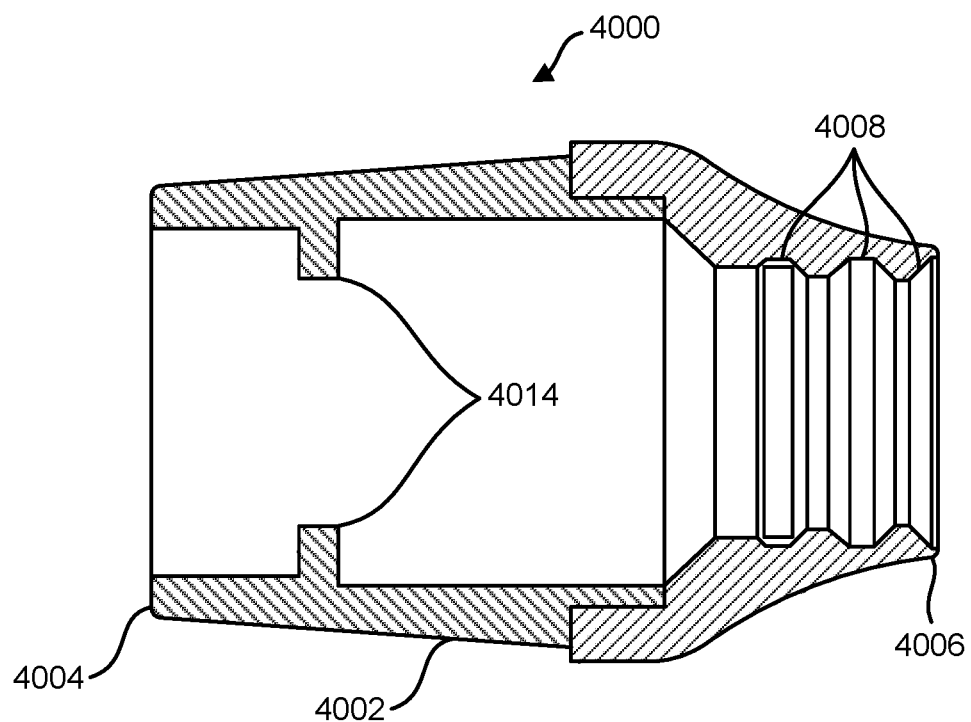
FIG. 36 is a partial cross-sectional side view of the band ligation apparatus of FIG. 33.

The proximal end 4003 is elastic for fitting over a distal end of various imaging devices, such as an endoscope. The proximal end 4003 has three elastic grooves or rings 4008 formed on an interior of the barrel 4002, for example as illustrated in FIG. 36, that can stretch to mate with distal ends of imaging devices having cross-sectional diameters of different sizes. Each ring 4008 can have a different diameter such that a distal-most ring has a smallest diameter and a proximal-most ring has a largest diameter. For example, a distal portion of a barrel of an imaging device with a smaller cross-sectional diameter can be inserted into the distal-most ring 4008 while the other rings 4008 stretch and grip onto the barrel of the imaging device proximal to the distal-most end of the imaging device, providing a secure fit. However, a barrel of an imaging device having a larger cross-sectional area may only be able to fit into the proximal-most ring 4008. As such, the apparatus 4000 can be used on imaging devices, such as endoscopes, of different sizes without having to adjust or change any proximal engagement mechanisms. Specific diameters, cross-sectional shapes, and axial spacing among the rings can vary depending on specific imaging devices to be used.

Two optional notches 4012 are formed on the distal end 4004 similar to notch 112. The notches 4012 are formed opposite each other around the circumference of the distal end 4004 and, similar to notch 112, act to engage each ligation band 4070 during deployment to help ensure even deployment. Each notch 4012 is formed by a distally-inward sloped surface on the outer surface of the barrel 4002 to define a rim 4012a. An alignment marker 4013 is formed on a proximal portion of the barrel 4002 in the form of a stripe of distinct color to help users align the apparatus 4000 when placing the proximal end 4006 onto an imaging device that may have more than one lumen (and thus may require a particular alignment to ensure a correct lumen has unrestricted access to the apparatus 4000). While notches are illustrated herein, ligation barrels can be provided having a crisscrossing or engaging pull cord orientation that do not include notches.

The barrel 4002 has two tissue-stopping features 4014 in the form of tabs that are similar to ledge 2020. The tissue-stopping features 4014 can extend radially inwardly from opposite sides of the inner surface of the barrel 4002 and can allow pull cords 4050, 4060 to extend therethrough while stopping tissue from being retracted too far into the barrel 4002. The tissue-stopping features 4014 can extend perpendicularly to the axis L2, similar to the angle of the distal end 4004.

Figure 37:
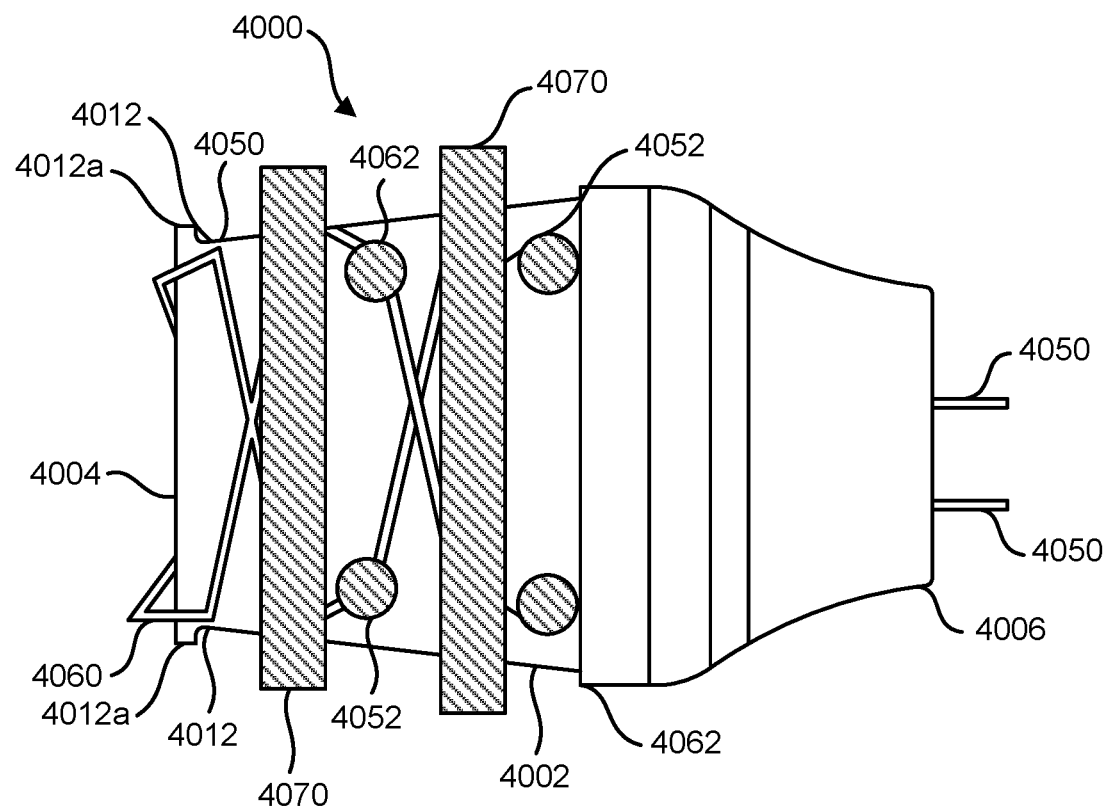
FIG. 37 is a side view of the band ligation apparatus of FIG. 33.
Figure 38:
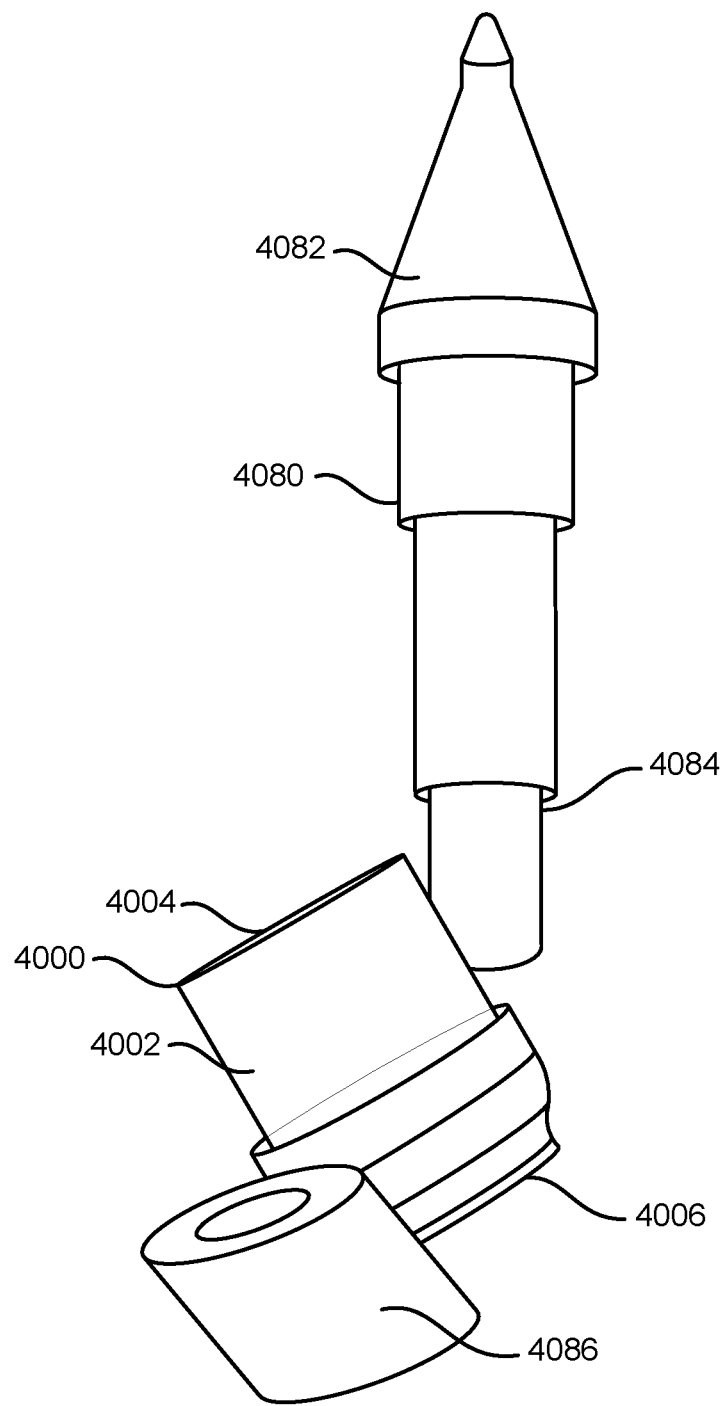
FIG. 38 is a side perspective view of another embodiment of a loading apparatus with the band ligation apparatus of FIG. 33.
Figure 39:
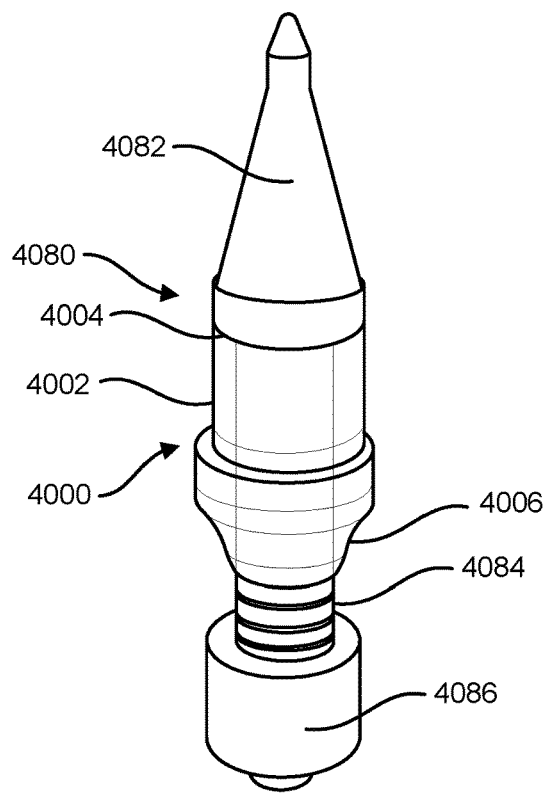
FIG. 39 is a side perspective view of the loading apparatus of FIG. 38 engaged with the band ligation apparatus of FIG. 33.
Figure 40:
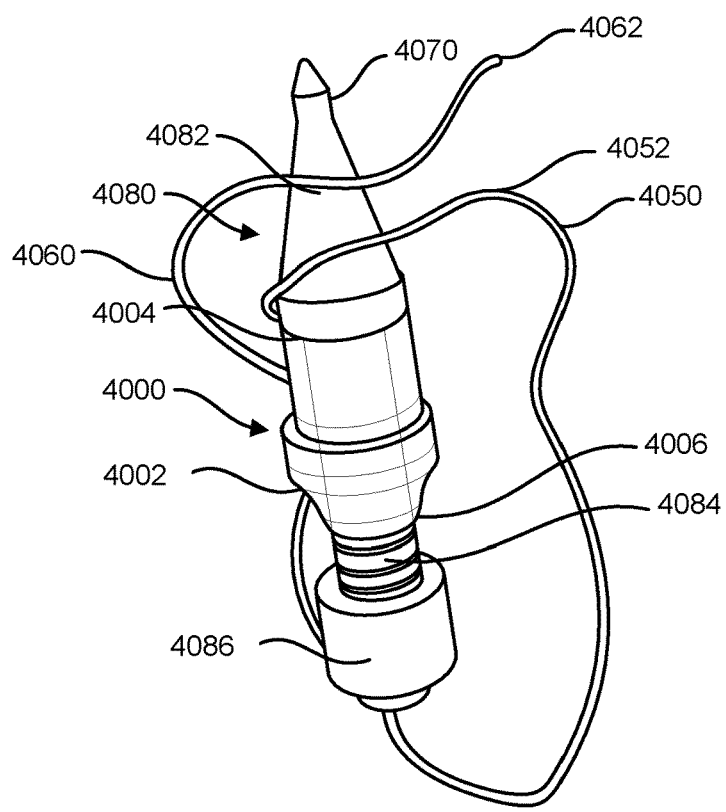
FIG. 40 is a side perspective view of the loading apparatus of FIG. 38 engaged with the band ligation apparatus of FIG. 33.
Figure 41:
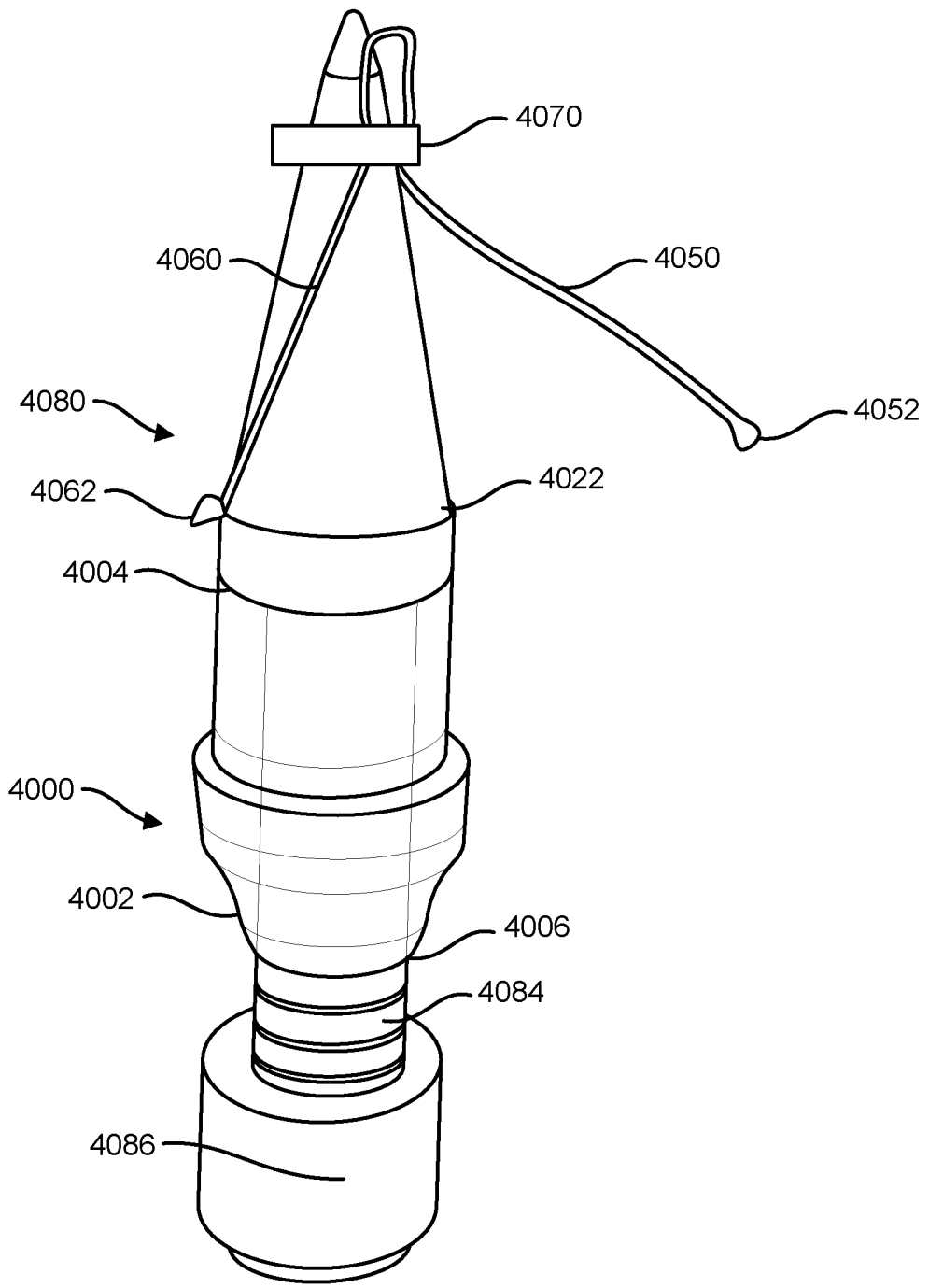
FIG. 41 is a side perspective view of the loading apparatus of FIG. 38 engaged with the band ligation apparatus of FIG. 33.

The apparatus 4000 can be loaded with pull cords 4050, 4060, beads 4052, 4062 disposed on the cords 4050, 4060, and ligation bands 4070 in the same crisscrossing or engaging approach as discussed above regarding apparatus 100, and as illustrated in the simplified representation in FIG. 37. As such, ligation bands 4070 can be deployed consistently and evenly from the straight distal end 4004 because the crisscrossing or engaging orientation of the cords 4050, 4060 causes a more even, central pulling force to be applied to the cords 4050, 4060 and allows for greater visibility through the barrel 4002 as a user draws the cords proximally through the barrel 4002 to deploy the bands 4070. The beads 4052, 4062 on each corresponding pull cord 4050, 4060 can be aligned on a same side of the outer surface of the barrel 4002 between the notches 4012 such that the beads 4052, 4062 can slide distally and loop around the distal end 4004 without interfering with the notches 4012 and the notches 4012 can engage and delay the bands 4070 without catching the beads 4052, 4062.

As illustrated in FIGS. 38-41, the apparatus 4000 can also be optionally loaded using a loading apparatus 4080 similar to loading apparatus 200. The loading apparatus 4080 has a conical head 4082, a shaft 4084, and a nut 4086. The loading apparatus can thus be attached to the apparatus 4000 in a similar manner to loading apparatus 200 attaching to band ligation apparatus 1000, and the ligation bands 4070 can be loaded onto apparatus 4000 in the same manner as discussed above.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A band ligation device, comprising:
   an elongate barrel having a proximal end matable to an endoscope, a distal end, and an inner lumen extending through the proximal and distal ends;
   a plurality of bands disposed circumferentially around an external surface of the elongate barrel; and
   first and second cords, each cord extending from a terminal trailing end distally along the external surface of the elongate barrel, around the distal end, and proximally through the inner lumen such that a leading end of the cord extends proximally from the inner lumen of the elongate barrel, the first and second cords overlapping one another to form a plurality of points of overlap in a crisscross pattern along the external surface, and the first and second cords having a plurality of beads immovably disposed thereon and positioned between each of the plurality of bands for deploying the bands, and
   wherein the elongate barrel has a horizontal plane extending along a longitudinal axis of the inner lumen and through the distal end defining first and second sides of the elongate barrel, and the crisscross pattern is formed only on one of the first and second sides of the elongate barrel.

2. The device of claim 1, wherein proximal retraction of the leading end of each of the first and second cords is configured to cause the plurality of beads to sequentially advance the plurality of bands distally to deploy the bands around tissue drawn into the inner lumen of the elongate barrel.

3. The device of claim 1, wherein the crisscross pattern of the first and second cords includes the first and second cords being looped around each other at each point of overlap by the first and second cords along the external surface.

4. The device of claim 1, wherein each point of overlap by the first and second cords along the external surface is arranged in a line on the external surface that extends parallel to the longitudinal axis of the inner lumen.

5. The device of claim 1, wherein the distal end of the elongate barrel has a terminal end surface extending at an oblique angle to the longitudinal axis of the inner lumen, the terminal end surface has a distal-most point, a proximal-most point, and first and second opposed mid-points positioned equidistant between the distal-most and proximal-most points, and the horizontal plane of the elongate barrel extends through the first and second opposed mid-points to define a first horizontal segment of the elongate barrel including the distal-most point, and a second horizontal segment of the elongate barrel including the proximal-most point.

6. The device of claim 5, wherein the terminal trailing end of each cord is positioned on the first horizontal segment of the elongate barrel, and wherein each cord extends distally from the terminal trailing end along only the first horizontal segment on the external surface of the elongate barrel.

7. The device of claim 1, wherein the elongate barrel includes at least one notch formed thereon adjacent the distal end, the at least one notch being configured to seat a band of the plurality of bands during deployment of the bands.

8. The device of claim 1, wherein the external surface of the elongate barrel has at least one lip formed adjacent the distal end of the elongate barrel configured to engage and delay deployment of each of the plurality of bands.

9. The device of claim 1, wherein the elongate barrel has at least one tissue-stopping protrusion projecting radially inward from an inner sidewall of the inner lumen.

10. A band ligation apparatus, comprising:
a hollow elongate barrel having a proximal end and a distal end with a terminal surface;
first and second cords extending through the hollow elongate barrel, around the terminal surface, and along an outer surface of the hollow elongate barrel, the first and second cords having a plurality of beads immovably disposed thereon; and
a plurality of bands disposed circumferentially around the hollow elongate barrel and the first and second cords, the plurality of bands being spaced axially therealong, at least one of the plurality of beads on each of the first and second cords being positioned between each of the plurality of bands for deploying the bands;
wherein the first and second cords engage one another between each of the plurality of bands along the outer surface.

11. The apparatus of claim 10, wherein the first and second cords are twisted together as they engage.

12. The apparatus of claim 10, wherein the first and second cords engage one another along the outer surface of the hollow elongate barrel in an approximately straight line parallel to a longitudinal axis of the hollow elongate barrel.

13. The apparatus of claim 10, wherein the terminal surface of the hollow elongate barrel has one of an oblique angle and a perpendicular angle relative to a longitudinal axis of the hollow elongate barrel.

14. The apparatus of claim 10, wherein the hollow elongate barrel has at least one ledge projecting radially inward from an inner sidewall of the hollow elongate barrel.

15. The band ligation apparatus of claim 10, wherein proximal retraction of the leading end of each of the first and second cords through the hollow elongate barrel is configured to cause the plurality of beads to sequentially advance the plurality of bands distally to deploy the bands around tissue drawn into the inner lumen of the elongate barrel.

16. A method for loading a plurality of bands onto a ligation barrel, comprising: positioning a first bead on a terminal end of a first cord at a first location on an outer surface of the ligation barrel, and positioning a second bead on a second cord at a second location on the outer surface of the ligation barrel, the first and second locations being spaced equidistant from a distal end of the ligation barrel relative to each other and being spaced circumferentially from each other on the ligation barrel; advancing a first band onto the ligation barrel to position the first band distally adjacent the first and second beads; after advancing the first band onto the ligation barrel, crossing the first and second cords at least once; positioning a third bead on the first cord longitudinally distal to one of the first and second beads and positioning a fourth bead on the second cord longitudinally distal to the other of the first and second beads; and advancing a second band onto the ligation barrel to position the second band distally adjacent the third and fourth beads.

17. The method of claim 16, further comprising: after advancing the second band onto the ligation barrel, crossing the first and second cords at least once; positioning a fifth bead on the first cord longitudinally distal to one of the third or fourth beads and positioning a sixth bead on the second cord longitudinally distal to the other of the third or fourth beads; and advancing a third band onto the ligation barrel to position the third band distally adjacent the fifth and sixth beads.

18. The method of claim 16, wherein crossing the first and second cords at least once includes twisting the first and second cords together at least one.

* * * * *